(12) United States Patent
Zhu et al.

(10) Patent No.: US 12,269,886 B2
(45) Date of Patent: Apr. 8, 2025

(54) TETRAVALENT BISPECIFIC ANTIBODY AGAINST PD-1 AND PD-L1

(71) Applicant: Sunshine Guojian Pharmaceutical (Shanghai) Co., Ltd., Shanghai (CN)

(72) Inventors: Zhenping Zhu, Shanghai (CN); Jie Zhao, Shanghai (CN); Haomin Huang, Shanghai (CN); Mengying Xia, Shanghai (CN)

(73) Assignee: Sunshine Guojian Pharmaceutical (Shanghai) Co., Ltd., Shanghai (CN)

(*) Notice: Subject to any disclaimer, the term of this patent is extended or adjusted under 35 U.S.C. 154(b) by 347 days.

(21) Appl. No.: 17/615,475

(22) PCT Filed: Apr. 19, 2021

(86) PCT No.: PCT/CN2021/088154
§ 371 (c)(1),
(2) Date: Nov. 30, 2021

(87) PCT Pub. No.: WO2021/227782
PCT Pub. Date: Nov. 18, 2021

(65) Prior Publication Data
US 2023/0076124 A1    Mar. 9, 2023

(30) Foreign Application Priority Data

May 15, 2020   (WO) ................ PCT/CN2020/090442

(51) Int. Cl.
| | | |
|---|---|---|
| C07K 16/28 | (2006.01) |
| A61K 39/00 | (2006.01) |
| A61P 35/00 | (2006.01) |
| C12N 5/10 | (2006.01) |
| C12N 15/00 | (2006.01) |
| C12N 15/11 | (2006.01) |

(52) U.S. Cl.
CPC .......... *C07K 16/2827* (2013.01); *A61P 35/00* (2018.01); *C07K 16/2818* (2013.01); *A61K 2039/505* (2013.01); *C07K 2317/24* (2013.01); *C07K 2317/31* (2013.01); *C07K 2317/35* (2013.01); *C07K 2317/76* (2013.01); *C07K 2317/92* (2013.01); *C12N 5/10* (2013.01); *C12N 15/00* (2013.01); *C12N 15/11* (2013.01); *C12N 2510/00* (2013.01); *C12N 2800/00* (2013.01)

(58) Field of Classification Search
CPC ........... C07K 16/2827; C07K 16/2818; C07K 2317/24; C07K 2317/31; C07K 2317/35; C07K 2317/76; C07K 2317/73; C07K 2317/56; A61P 35/00; A61P 35/02; A61K 2039/505
See application file for complete search history.

(56) References Cited

U.S. PATENT DOCUMENTS

| | | | |
|---|---|---|---|
| 10,927,185 B2 * | 2/2021 | Ito ..................... | C07K 16/2896 |
| 2015/0210769 A1 | 7/2015 | Freeman et al. | |
| 2018/0346571 A1 | 12/2018 | Gurney et al. | |

FOREIGN PATENT DOCUMENTS

| | | | |
|---|---|---|---|
| CN | 105612182 A | 5/2016 | |
| CN | 105820251 A | 8/2016 | |
| CN | 108136003 A | 6/2018 | |
| CN | 108697791 A | 10/2018 | |
| CN | 109563166 A | 4/2019 | |
| CN | 110382549 A | 10/2019 | |
| CN | 110520445 A | 11/2019 | |
| CN | 110914306 A | 3/2020 | |
| WO | 2007044887 A2 | 4/2007 | |
| WO | WO-2018137576 A1 * | 8/2018 | ............. A61P 31/00 |
| WO | 2019190327 A2 | 10/2019 | |

OTHER PUBLICATIONS

Blarcom T.V. et al. "Engineering a Bispecific Antibody with a Common Light Chain: Identification and Optimization of an Anti-CD3 Epsilon and Anti-GPC3 Bispecific Antibody, ERY97 4", Methods, vol. 154, Oct. 13, 2018, pp. 10-20.
Blarcom T.V. et al. "Productive Common Light Chain Libraries Yield Diverse Panels of High Affinity Bispecific Antibodies", MABS, vol. 10, No. 2, Dec. 14, 2017, pp. 256-268.
International Search Report for International Application No. PCT/CN2021/088153 mailed Jul. 22, 2021.

* cited by examiner

*Primary Examiner* — Hong Sang
*Assistant Examiner* — Carol Ann Chase
(74) *Attorney, Agent, or Firm* — Morse, Barnes-Brown & Pendleton, P.C.; Martin Z. Zhang; Russell L. Widom

(57) ABSTRACT

Provided are an antibody that binds to human PD-L1, and a tetravalent bispecific antibody against PD-1 and PD-L1 constructed based on the antibody that binds to human PD-L1. The tetravalent bispecific antibody requires no Fc modification, has no mismatch problems, and the preparation method thereof is simple. The biological activities and physical and chemical properties of the tetravalent bispecific antibody are similar with or even better than those of the monoclonal antibodies.

10 Claims, 12 Drawing Sheets

Specification includes a Sequence Listing.

SEQUENCE LISTING

```
<160> NUMBER OF SEQ ID NOS: 32

<210> SEQ ID NO 1
<211> LENGTH: 5
<212> TYPE: PRT
<213> ORGANISM: Mus musculus

<400> SEQUENCE: 1

Ser Tyr Gly Val His
1               5

<210> SEQ ID NO 2
<211> LENGTH: 16
<212> TYPE: PRT
<213> ORGANISM: Mus musculus

<400> SEQUENCE: 2

Leu Ile Trp Ser Gly Gly Gly Thr Asp Tyr Asn Ala Ala Phe Ile Ser
1               5                   10                  15

<210> SEQ ID NO 3
<211> LENGTH: 9
<212> TYPE: PRT
<213> ORGANISM: Mus musculus

<400> SEQUENCE: 3

Gln Leu Gly Leu Arg Ala Met Asp Tyr
1               5

<210> SEQ ID NO 4
<211> LENGTH: 11
<212> TYPE: PRT
<213> ORGANISM: Mus musculus

<400> SEQUENCE: 4

Arg Ala Ser Gln Ser Ile Gly Thr Thr Ile His
1               5                   10

<210> SEQ ID NO 5
<211> LENGTH: 7
<212> TYPE: PRT
<213> ORGANISM: Mus musculus

<400> SEQUENCE: 5

Tyr Ala Ser Glu Ser Val Ser
1               5

<210> SEQ ID NO 6
<211> LENGTH: 9
<212> TYPE: PRT
<213> ORGANISM: Mus musculus

<400> SEQUENCE: 6

Gln Gln Ser Asn Ser Trp Pro Leu Thr
1               5

<210> SEQ ID NO 7
```

```
<211> LENGTH: 11
<212> TYPE: PRT
<213> ORGANISM: Artificial
<220> FEATURE:
<223> OTHER INFORMATION: The fourth framework region of heavy chain

<400> SEQUENCE: 7

Trp Gly Gln Gly Thr Ser Val Thr Val Ser Ser
1               5                   10

<210> SEQ ID NO 8
<211> LENGTH: 10
<212> TYPE: PRT
<213> ORGANISM: Artificial
<220> FEATURE:
<223> OTHER INFORMATION: The fourth framework region of light chain

<400> SEQUENCE: 8

Phe Gly Ala Gly Thr Lys Leu Glu Ile Lys
1               5                   10

<210> SEQ ID NO 9
<211> LENGTH: 117
<212> TYPE: PRT
<213> ORGANISM: Artificial
<220> FEATURE:
<223> OTHER INFORMATION: Amino acid sequence of heavy chain variable
      region of Anti-PDL1

<400> SEQUENCE: 9

Gln Val Gln Leu Gln Gln Ser Gly Gly Gly Leu Val Lys Pro Ser Gln
1               5                   10                  15

Ser Leu Ser Leu Thr Cys Thr Val Ser Gly Phe Ser Leu Thr Ser Tyr
                20                  25                  30

Gly Val His Trp Val Arg Gln Pro Pro Gly Lys Gly Leu Glu Trp Ile
            35                  40                  45

Gly Leu Ile Trp Ser Gly Gly Gly Thr Asp Tyr Asn Pro Ser Leu Lys
        50                  55                  60

Ser Arg Leu Thr Ile Ser Arg Asp Thr Ser Lys Asn Gln Val Ser Phe
65                  70                  75                  80

Lys Ile Ser Ser Leu Thr Ala Ala Asp Thr Ala Val Tyr Tyr Cys Ala
                85                  90                  95

Arg Gln Leu Gly Leu Arg Ala Met Asp Tyr Trp Gly Gln Gly Thr Ser
            100                 105                 110

Val Thr Val Ser Ser
        115

<210> SEQ ID NO 10
<211> LENGTH: 107
<212> TYPE: PRT
<213> ORGANISM: Artificial
<220> FEATURE:
<223> OTHER INFORMATION: Amino acid sequence of light chain variable
      region of Anti-PDL1

<400> SEQUENCE: 10

Glu Ile Val Leu Thr Gln Ser Pro Asp Phe Leu Ser Val Thr Pro Lys
1               5                   10                  15

Glu Lys Val Thr Ile Thr Cys Arg Ala Ser Gln Ser Ile Gly Thr Thr
                20                  25                  30

Ile His Trp Tyr Gln Gln Lys Pro Asp Gln Ser Pro Lys Leu Leu Ile
            35                  40                  45
```

```
Lys Tyr Ala Ser Gln Ser Phe Ser Gly Val Pro Ser Arg Phe Ser Gly
    50                  55                  60

Ser Gly Ser Gly Thr Asp Phe Thr Leu Thr Ile Asn Ser Val Glu Ala
65                  70                  75                  80

Glu Asp Ala Ala Thr Tyr Tyr Cys Gln Gln Ser Asn Ser Trp Pro Leu
                85                  90                  95

Thr Phe Gly Ala Gly Thr Lys Leu Glu Ile Lys
            100                 105
```

<210> SEQ ID NO 11
<211> LENGTH: 330
<212> TYPE: PRT
<213> ORGANISM: Artificial
<220> FEATURE:
<223> OTHER INFORMATION: Amino acid sequence of heavy chain constant
      region of human IgG1

<400> SEQUENCE: 11

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300
```

```
Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 12
<211> LENGTH: 107
<212> TYPE: PRT
<213> ORGANISM: Artificial
<220> FEATURE:
<223> OTHER INFORMATION: Amino acid sequence of human Kappa light chain
      constant region

<400> SEQUENCE: 12

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 13
<211> LENGTH: 447
<212> TYPE: PRT
<213> ORGANISM: Artificial
<220> FEATURE:
<223> OTHER INFORMATION: Amino acid sequence of heavy chain of Anti-PDL1

<400> SEQUENCE: 13

Gln Val Gln Leu Gln Gln Ser Gly Gly Gly Leu Val Lys Pro Ser Gln
1               5                   10                  15

Ser Leu Ser Leu Thr Cys Thr Val Ser Gly Phe Ser Leu Thr Ser Tyr
            20                  25                  30

Gly Val His Trp Val Arg Gln Pro Pro Gly Lys Gly Leu Glu Trp Ile
        35                  40                  45

Gly Leu Ile Trp Ser Gly Gly Thr Asp Tyr Asn Pro Ser Leu Lys
    50                  55                  60

Ser Arg Leu Thr Ile Ser Arg Asp Thr Ser Lys Asn Gln Val Ser Phe
65                  70                  75                  80

Lys Ile Ser Ser Leu Thr Ala Ala Asp Thr Ala Val Tyr Tyr Cys Ala
                85                  90                  95

Arg Gln Leu Gly Leu Arg Ala Met Asp Tyr Trp Gly Gln Gly Thr Ser
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160
```

```
Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
            325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445
```

<210> SEQ ID NO 14
<211> LENGTH: 1341
<212> TYPE: DNA
<213> ORGANISM: Artificial
<220> FEATURE:
<223> OTHER INFORMATION: Nucleotide sequence of heavy chain of Anti-PDL1

<400> SEQUENCE: 14

```
caggtccagc tgcagcagtc aggaggggggc ctggtgaagc catcacagag cctgtccctg      60
acctgcacag tctctgggtt cagtctgact tcatacggag tgcactgggt ccgacagccc     120
cctggaaagg gactggagtg gatcggcctg atttggtctg gcggggggaac agactataac     180 ccagcctga atcccggct gaccatctct agagatacca gtaagaatca agtgagcttt      240
aaaattagct ccctgacagc cgctgacact gcagtgtact attgtgcaag gcagctggga      300
ctgcgagcta tggattactg gggacaggggc acttccgtga ccgtctctag tgcgagcacc     360
aagggacctt ccgtgtttcc cctcgccccc agctccaaaa gcaccagcgg cggaacagct     420
gctctcggct gtctcgtcaa ggattacttc cccgagcccg tgaccgtgag ctggaacagc     480
```

```
ggagccctga caagcggcgt ccacaccttc cctgctgtcc tacagtcctc cggactgtac    540
agcctgagca gcgtggtgac agtccctagc agctccctgg gcacccagac atatatttgc    600
aacgtgaatc acaagcccag caacaccaag gtcgataaga aggtggagcc taagtcctgc    660
gacaagaccc acacatgtcc ccctgtcccg gctcctgaac tgctgggagg cccttccgtg    720
ttcctgttcc cccctaagcc caaggacacc ctgatgattt ccaggacacc cgaggtgacc    780
tgtgtggtgg tggacgtcag ccacgaggac cccgaggtga aattcaactg gtacgtcgat    840
ggcgtggagg tgcacaacgc taagaccaag cccagggagg agcagtacaa ttccacctac    900
agggtggtgt ccgtgctgac cgtcctccat caggactggc tgaacggcaa agagtataag    960
tgcaaggtga gcaacaaggc cctccctgct cccatcgaga agaccatcag caaagccaag   1020
ggccagccca gggaacctca gtctataccc tgcctcccag caggaggga gatgaccaag   1080 aaccaagtga gcctcacatg cctcgtcaag ggcttctatc cttccgatat tgccgtcgag   1140
tgggagtcca acggacagcc cgagaacaac tacaagacaa cccccccgt gctcgattcc   1200 gatggcagct tcttcctgta ctccaagctg accgtggaca gtccagatg caacaaggc   1260 aacgtcttca gttgcagcgt catgcatgag gccctccaca accactacac ccagaagagc   1320
ctctccctga gccctggaaa g                                             1341
```

<210> SEQ ID NO 15
<211> LENGTH: 214
<212> TYPE: PRT
<213> ORGANISM: Artificial
<220> FEATURE:
<223> OTHER INFORMATION: Amino acid sequence of light chain of Anti-PDL1

<400> SEQUENCE: 15

```
Glu Ile Val Leu Thr Gln Ser Pro Asp Phe Leu Ser Val Thr Pro Lys
1               5                   10                  15

Glu Lys Val Thr Ile Thr Cys Arg Ala Ser Gln Ser Ile Gly Thr Thr
            20                  25                  30

Ile His Trp Tyr Gln Gln Lys Pro Asp Gln Ser Pro Lys Leu Leu Ile
        35                  40                  45

Lys Tyr Ala Ser Gln Ser Phe Ser Gly Val Pro Ser Arg Phe Ser Gly
    50                  55                  60

Ser Gly Ser Gly Thr Asp Phe Thr Leu Thr Ile Asn Ser Val Glu Ala
65                  70                  75                  80

Glu Asp Ala Ala Thr Tyr Tyr Cys Gln Gln Ser Asn Ser Trp Pro Leu
                85                  90                  95

Thr Phe Gly Ala Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

Phe Asn Arg Gly Glu Cys
    210

<210> SEQ ID NO 16
<211> LENGTH: 642
<212> TYPE: DNA
<213> ORGANISM: Artificial
<220> FEATURE:
<223> OTHER INFORMATION: Nucleotide sequence of light chain of Anti-PDL1

<400> SEQUENCE: 16

```
gaaatcgtgc tgacacagag ccctgacttt ctgtccgtga cacccaagga gaaagtcact     60
atcacctgcc gggctagcca gtccatcgga accacaattc actggtacca gcagaagccc    120
gaccagagcc ctaagctgct gattaaatat gcctctcaga gtttctcagg cgtgccatcc    180
agatttagcg gctccgggtc tggaactgac ttcacactga ctatcaactc tgtcgaggca    240
gaagatgccg ctacctacta ttgtcagcag agtaattcat ggcccctgac ctttggcgcc    300
gggacaaagc tggaaattaa agaaccgtc gccgctccca gcgtcttcat cttcccccc     360
agcgatgagc agctgaagag cggaaccgcc agcgtggtgt gcctgctgaa caacttctac    420
cccagggagg ccaaggtgca atggaaggtg acaacgccc tacagagcgg caactcccag    480
gagagcgtga ccgagcagga cagcaaggat agcacctaca gcctgagcag caccctcacc    540
ctgagcaagg ccgactacga aagcacaag gtgtacgcct gcgaggtgac ccatcagggc    600
ctgagcagcc ctgtgaccaa gagcttcaac aggggcgagt gc                       642
```

<210> SEQ ID NO 17
<211> LENGTH: 5
<212> TYPE: PRT
<213> ORGANISM: Artificial
<220> FEATURE:
<223> OTHER INFORMATION: Amino acid sequence of heavy chain
      complementarity determining region H-CDR1 of Anti-PDL1

<400> SEQUENCE: 17

Ser Tyr Gly Val His
1               5

<210> SEQ ID NO 18
<211> LENGTH: 16
<212> TYPE: PRT
<213> ORGANISM: Artificial
<220> FEATURE:
<223> OTHER INFORMATION: Amino acid sequence of heavy chain
      complementarity determining region H-CDR2 of Anti-PDL1

<400> SEQUENCE: 18

Leu Ile Trp Ser Gly Gly Gly Thr Asp Tyr Asn Pro Ser Leu Lys Ser
1               5                   10                  15

<210> SEQ ID NO 19
<211> LENGTH: 9
<212> TYPE: PRT
<213> ORGANISM: Artificial
<220> FEATURE:
<223> OTHER INFORMATION: Amino acid sequence of heavy chain
      complementarity determining region H-CDR3 of Anti-PDL1

<400> SEQUENCE: 19

Gln Leu Gly Leu Arg Ala Met Asp Tyr
1               5

```
<210> SEQ ID NO 20
<211> LENGTH: 11
<212> TYPE: PRT
<213> ORGANISM: Artificial
<220> FEATURE:
<223> OTHER INFORMATION: Amino acid sequence of light chain
      complementarity determining region L-CDR1 of Anti-PDL1

<400> SEQUENCE: 20

Arg Ala Ser Gln Ser Ile Gly Thr Thr Ile His
1               5                   10

<210> SEQ ID NO 21
<211> LENGTH: 7
<212> TYPE: PRT
<213> ORGANISM: Artificial
<220> FEATURE:
<223> OTHER INFORMATION: Amino acid sequence of light chain
      complementarity determining region L-CDR2 of Anti-PDL1

<400> SEQUENCE: 21

Tyr Ala Ser Gln Ser Phe Ser
1               5

<210> SEQ ID NO 22
<211> LENGTH: 9
<212> TYPE: PRT
<213> ORGANISM: Artificial
<220> FEATURE:
<223> OTHER INFORMATION: Amino acid sequence of light chain
      complementarity determining region L-CDR3 of Anti-PDL1

<400> SEQUENCE: 22

Gln Gln Ser Asn Ser Trp Pro Leu Thr
1               5

<210> SEQ ID NO 23
<211> LENGTH: 118
<212> TYPE: PRT
<213> ORGANISM: Artificial
<220> FEATURE:
<223> OTHER INFORMATION: Amino acid sequence of heavy chain variable
      region of Atezolizumab

<400> SEQUENCE: 23

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser
        115

<210> SEQ ID NO 24
<211> LENGTH: 107
```

```
<212> TYPE: PRT
<213> ORGANISM: Artificial
<220> FEATURE:
<223> OTHER INFORMATION: Amino acid sequence of light chain variable
      region of Atezolizumab

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys
            100                 105

<210> SEQ ID NO 25
<211> LENGTH: 117
<212> TYPE: PRT
<213> ORGANISM: Artificial
<220> FEATURE:
<223> OTHER INFORMATION: Amino acid sequence of heavy chain variable
      region of mAb1-25-Hu (609)

<400> SEQUENCE: 25

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Ser Tyr
            20                  25                  30

Asp Met Ser Trp Val Arg Gln Ala Pro Gly Lys Arg Leu Glu Trp Val
        35                  40                  45

Ala Thr Ile Ser Gly Gly Gly Arg Tyr Thr Tyr Tyr Pro Asp Thr Val
    50                  55                  60

Lys Gly Arg Phe Thr Ile Ser Arg Asp Asn Ala Lys Asn Ser His Tyr
65                  70                  75                  80

Leu Gln Met Asn Ser Leu Arg Ala Glu Asp Thr Ala Val Tyr Phe Cys
                85                  90                  95

Ala Ser Pro Tyr Gly Gly Tyr Phe Asp Val Trp Gly Gln Gly Thr Leu
            100                 105                 110

Val Thr Val Ser Ser
        115

<210> SEQ ID NO 26
<211> LENGTH: 107
<212> TYPE: PRT
<213> ORGANISM: Artificial
<220> FEATURE:
<223> OTHER INFORMATION: Amino acid sequence of light chain variable
      region of mAb1-25-Hu (609)

<400> SEQUENCE: 26

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Asn Phe
```

```
                    20                  25                  30
Leu His Trp Tyr Gln Gln Lys Pro Gly Gln Ala Pro Arg Leu Leu Ile
                35                  40                  45

Lys Tyr Ala Ser Gln Ser Ile Ser Gly Ile Pro Ala Arg Phe Ser Gly
            50                  55                  60

Ser Gly Ser Gly Thr Asp Phe Thr Leu Thr Ile Ser Ser Leu Glu Pro
65                  70                  75                  80

Glu Asp Phe Ala Val Tyr Phe Cys Gln Gln Ser Asn Ser Trp Pro His
                85                  90                  95

Thr Phe Gly Gln Gly Thr Lys Val Glu Ile Lys
                100                 105
```

<210> SEQ ID NO 27
<211> LENGTH: 327
<212> TYPE: PRT
<213> ORGANISM: Artificial
<220> FEATURE:
<223> OTHER INFORMATION: Amino acid sequence of heavy chain constant region of IgG4 (S228P)

<400> SEQUENCE: 27

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
                100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270
```

```
Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 28
<211> LENGTH: 15
<212> TYPE: PRT
<213> ORGANISM: Artificial
<220> FEATURE:
<223> OTHER INFORMATION: Linker (GGGGSGGGGSGGGGS)

<400> SEQUENCE: 28

Gly Gly Gly Gly Ser Gly Gly Gly Gly Ser Gly Gly Gly Gly Ser
1               5                   10                  15

<210> SEQ ID NO 29
<211> LENGTH: 674
<212> TYPE: PRT
<213> ORGANISM: Artificial
<220> FEATURE:
<223> OTHER INFORMATION: Amino acid sequence of PDL1-Fab-609-IgG4

<400> SEQUENCE: 29

Gln Val Gln Leu Gln Gln Ser Gly Gly Gly Leu Val Lys Pro Ser Gln
1               5                   10                  15

Ser Leu Ser Leu Thr Cys Thr Val Ser Gly Phe Ser Leu Thr Ser Tyr
            20                  25                  30

Gly Val His Trp Val Arg Gln Pro Pro Gly Lys Gly Leu Glu Trp Ile
        35                  40                  45

Gly Leu Ile Trp Ser Gly Gly Gly Thr Asp Tyr Asn Pro Ser Leu Lys
    50                  55                  60

Ser Arg Leu Thr Ile Ser Arg Asp Thr Ser Lys Asn Gln Val Ser Phe
65                  70                  75                  80

Lys Ile Ser Ser Leu Thr Ala Ala Asp Thr Ala Val Tyr Tyr Cys Ala
                85                  90                  95

Arg Gln Leu Gly Leu Arg Ala Met Asp Tyr Trp Gly Gln Gly Thr Ser
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Gly Gly Gly Ser Gly Gly Gly Gly
    210                 215                 220

Ser Gly Gly Gly Gly Ser Glu Val Lys Leu Val Glu Ser Gly Gly Gly
225                 230                 235                 240
```

```
Leu Val Gln Pro Gly Gly Ser Leu Arg Leu Ser Cys Ala Ala Ser Gly
                245                 250                 255

Phe Ala Phe Ser Ser Tyr Asp Met Ser Trp Val Arg Gln Ala Pro Gly
            260                 265                 270

Lys Arg Leu Glu Trp Val Ala Thr Ile Ser Gly Gly Gly Arg Tyr Thr
        275                 280                 285

Tyr Tyr Pro Asp Thr Val Lys Gly Arg Phe Thr Ile Ser Arg Asp Asn
    290                 295                 300

Ala Lys Asn Ser His Tyr Leu Gln Met Asn Ser Leu Arg Ala Glu Asp
305                 310                 315                 320

Thr Ala Val Tyr Phe Cys Ala Ser Pro Tyr Gly Gly Tyr Phe Asp Val
                325                 330                 335

Trp Gly Gln Gly Thr Leu Val Thr Val Ser Ser Ala Ser Thr Lys Gly
            340                 345                 350

Pro Ser Val Phe Pro Leu Ala Pro Cys Ser Arg Ser Thr Ser Glu Ser
        355                 360                 365

Thr Ala Ala Leu Gly Cys Leu Val Lys Asp Tyr Phe Pro Glu Pro Val
    370                 375                 380

Thr Val Ser Trp Asn Ser Gly Ala Leu Thr Ser Gly Val His Thr Phe
385                 390                 395                 400

Pro Ala Val Leu Gln Ser Ser Gly Leu Tyr Ser Leu Ser Ser Val Val
                405                 410                 415

Thr Val Pro Ser Ser Ser Leu Gly Thr Lys Thr Tyr Thr Cys Asn Val
            420                 425                 430

Asp His Lys Pro Ser Asn Thr Lys Val Asp Lys Arg Val Glu Ser Lys
        435                 440                 445

Tyr Gly Pro Pro Cys Pro Pro Cys Pro Ala Pro Glu Phe Leu Gly Gly
    450                 455                 460

Pro Ser Val Phe Leu Phe Pro Pro Lys Pro Lys Asp Thr Leu Met Ile
465                 470                 475                 480

Ser Arg Thr Pro Glu Val Thr Cys Val Val Val Asp Val Ser Gln Glu
                485                 490                 495

Asp Pro Glu Val Gln Phe Asn Trp Tyr Val Asp Gly Val Glu Val His
            500                 505                 510

Asn Ala Lys Thr Lys Pro Arg Glu Glu Gln Phe Asn Ser Thr Tyr Arg
        515                 520                 525

Val Val Ser Val Leu Thr Val Leu His Gln Asp Trp Leu Asn Gly Lys
    530                 535                 540

Glu Tyr Lys Cys Lys Val Ser Asn Lys Gly Leu Pro Ser Ser Ile Glu
545                 550                 555                 560

Lys Thr Ile Ser Lys Ala Lys Gly Gln Pro Arg Glu Pro Gln Val Tyr
                565                 570                 575

Thr Leu Pro Pro Ser Gln Glu Glu Met Thr Lys Asn Gln Val Ser Leu
            580                 585                 590

Thr Cys Leu Val Lys Gly Phe Tyr Pro Ser Asp Ile Ala Val Glu Trp
        595                 600                 605

Glu Ser Asn Gly Gln Pro Glu Asn Asn Tyr Lys Thr Thr Pro Pro Val
    610                 615                 620

Leu Asp Ser Asp Gly Ser Phe Phe Leu Tyr Ser Arg Leu Thr Val Asp
625                 630                 635                 640

Lys Ser Arg Trp Gln Glu Gly Asn Val Phe Ser Cys Ser Val Met His
                645                 650                 655
```

Glu Ala Leu His Asn His Tyr Thr Gln Lys Ser Leu Ser Leu Ser Leu
        660                 665                 670

Gly Lys

<210> SEQ ID NO 30
<211> LENGTH: 2022
<212> TYPE: DNA
<213> ORGANISM: Artificial
<220> FEATURE:
<223> OTHER INFORMATION: Nucleotide sequence of PDL1-Fab-609-IgG4

<400> SEQUENCE: 30

| | | | | |
|---|---|---|---|---|
| caggtccagc | tgcagcagtc | aggaggggc | ctggtgaagc | catcacagag cctgtccctg | 60 |
| acctgcacag | tctctgggtt | cagtctgact | tcatacggag | tgcactgggt ccgacagccc | 120 |
| cctggaaagg | gactggagtg | gatcggcctg | atttggtctg | gcgggggaac agactataac | 180 |
| cccagcctga | atcccggct | gaccatctct | agagatacca | gtaagaatca agtgagcttt | 240 |
| aaaattagct | ccctgacagc | cgctgacact | gcagtgtact | attgtgcaag gcagctggga | 300 |
| ctgcgagcta | tggattactg | gggacagggc | acttccgtga | ccgtctctag tgcaagtacc | 360 |
| aagggaccta | gtgttttccc | tcttgcacct | tgctccaggt | caacatcaga gtccacagct | 420 |
| gctcttggat | gtctcgttaa | ggactacttc | ccagagccag | ttaccgtatc ctggaactcc | 480 |
| ggagctttga | caagcggcgt | tcatacattc | ccagctgtgt | tgcagagttc tgggttgtac | 540 |
| agtttgagct | cagtggtgac | cgtgccttca | tcttctttgg | gcactaagac ctacacctgc | 600 |
| aacgtggatc | acaagccaag | caacaccaag | gtggataaga | gggtgggtgg aggcggttca | 660 |
| ggcggaggtg | gcagcggagg | tggcgggagt | gaggtcaagc | tggtggaaag cggcggcggc | 720 |
| ctggtgcagc | ctggaggatc | cctgcggctg | agctgcgctg | cctccggctt cgctttcagc | 780 |
| tcctatgaca | tgtcctgggt | gaggcaggcc | cctggaaaga | ggctggagtg gtggctacc | 840 |
| atctccggag | gcggaaggta | cacctactac | cccgacacag | tgaagggaag gttcaccatc | 900 |
| agccgggata | cgccaaaaa | cagccactat | ctccagatga | actccctgag ggccgaagat | 960 |
| acagccgtgt | atttctgtgc | ctcccctac | ggaggctatt | ttgacgtgtg gggacagggc | 1020 |
| accctggtga | ccgtctcctc | cgcaagtacc | aagggaccta | gtgttttccc tcttgcacct | 1080 |
| tgctccaggt | caacatcaga | gtccacagct | gctcttggat | gtctcgttaa ggactacttc | 1140 |
| ccagagccag | ttaccgtatc | ctggaactcc | ggagctttga | caagcggcgt tcatacattc | 1200 |
| ccagctgtgt | tgcagagttc | tgggttgtac | agtttgagct | cagtggtgac cgtgccttca | 1260 |
| tcttctttgg | gcactaagac | ctacacctgc | aacgtggatc | acaagccaag caacaccaag | 1320 |
| gtggataaga | gggtggagtc | caagtacggc | ccaccatgtc | ctccatgtcc agcccctgaa | 1380 |
| ttttgggcg | gccttctgt | ctttctgttt | cctcctaaac | ctaaagatac cctgatgatc | 1440 |
| agccgcacac | ccgaagtcac | ttgtgtggtc | gtggatgtgt | ctcaggaaga tcccgaagtg | 1500 |
| cagtttaact | ggtatgtcga | tggcgtggaa | gtgcataatg | ccaaaactaa gccccgcgaa | 1560 |
| gaacagttca | acagcactta | tcgggtcgtg | tctgtgctca | cagtcctcca tcaggattgg | 1620 |
| ctgaatggga | agaatataa | gtgcaaggtg | agcaataagg | gcctcccag cagcatcgag | 1680 |
| aagactatta | gcaaagccaa | agggcagcca | cgggaacccc | agtgtacac tctgcccccc | 1740 |
| tctcaggagg | agatgactaa | aaatcaggtc | tctctgactt | gtctggtgaa agggtttat | 1800 |
| cccagcgaca | ttgccgtgga | gtgggagtct | aatggccagc | ccgagaataa ttataagaca | 1860 |
| actccccccg | tcctggactc | tgacggcagc | ttttcctgt | attctcggct gacagtggac | 1920 |

-continued

```
aaaagtcgct ggcaggaggg caatgtcttt agttgcagtg tcatgcatga ggccctgcac    1980
aatcactata cacagaaaag cctgtctctg agtctgggca aa                       2022
```

<210> SEQ ID NO 31
<211> LENGTH: 674
<212> TYPE: PRT
<213> ORGANISM: Artificial
<220> FEATURE:
<223> OTHER INFORMATION: Amino acid sequence of 609-Fab-PDL1-IgG4

<400> SEQUENCE: 31

| | | | | | | | | | | | | | | |
|---|---|---|---|---|---|---|---|---|---|---|---|---|---|---|
| Glu | Val | Lys | Leu | Val | Glu | Ser | Gly | Gly | Gly | Leu | Val | Gln | Pro | Gly | Gly |
| 1 | | | | 5 | | | | | 10 | | | | | 15 | |
| Ser | Leu | Arg | Leu | Ser | Cys | Ala | Ala | Ser | Gly | Phe | Ala | Phe | Ser | Ser | Tyr |
| | | | 20 | | | | | 25 | | | | | 30 | | |
| Asp | Met | Ser | Trp | Val | Arg | Gln | Ala | Pro | Gly | Lys | Arg | Leu | Glu | Trp | Val |
| | | 35 | | | | | 40 | | | | | 45 | | | |
| Ala | Thr | Ile | Ser | Gly | Gly | Gly | Arg | Tyr | Thr | Tyr | Tyr | Pro | Asp | Thr | Val |
| | 50 | | | | | 55 | | | | | 60 | | | | |
| Lys | Gly | Arg | Phe | Thr | Ile | Ser | Arg | Asp | Asn | Ala | Lys | Asn | Ser | His | Tyr |
| 65 | | | | | 70 | | | | | 75 | | | | | 80 |
| Leu | Gln | Met | Asn | Ser | Leu | Arg | Ala | Glu | Asp | Thr | Ala | Val | Tyr | Phe | Cys |
| | | | | 85 | | | | | 90 | | | | | 95 | |
| Ala | Ser | Pro | Tyr | Gly | Gly | Tyr | Phe | Asp | Val | Trp | Gly | Gln | Gly | Thr | Leu |
| | | | 100 | | | | | 105 | | | | | 110 | | |
| Val | Thr | Val | Ser | Ser | Ala | Ser | Thr | Lys | Gly | Pro | Ser | Val | Phe | Pro | Leu |
| | | 115 | | | | | 120 | | | | | 125 | | | |
| Ala | Pro | Cys | Ser | Arg | Ser | Thr | Ser | Glu | Ser | Thr | Ala | Ala | Leu | Gly | Cys |
| | 130 | | | | | 135 | | | | | 140 | | | | |
| Leu | Val | Lys | Asp | Tyr | Phe | Pro | Glu | Pro | Val | Thr | Val | Ser | Trp | Asn | Ser |
| 145 | | | | | 150 | | | | | 155 | | | | | 160 |
| Gly | Ala | Leu | Thr | Ser | Gly | Val | His | Thr | Phe | Pro | Ala | Val | Leu | Gln | Ser |
| | | | | 165 | | | | | 170 | | | | | 175 | |
| Ser | Gly | Leu | Tyr | Ser | Leu | Ser | Ser | Val | Val | Thr | Val | Pro | Ser | Ser | Ser |
| | | | 180 | | | | | 185 | | | | | 190 | | |
| Leu | Gly | Thr | Lys | Thr | Tyr | Thr | Cys | Asn | Val | Asp | His | Lys | Pro | Ser | Asn |
| | | 195 | | | | | 200 | | | | | 205 | | | |
| Thr | Lys | Val | Asp | Lys | Arg | Val | Gly | Gly | Gly | Ser | Gly | Gly | Gly | Gly |
| | 210 | | | | | 215 | | | | | 220 | | | | |
| Ser | Gly | Gly | Gly | Gly | Ser | Gln | Val | Gln | Leu | Gln | Gln | Ser | Gly | Gly | Gly |
| 225 | | | | | 230 | | | | | 235 | | | | | 240 |
| Leu | Val | Lys | Pro | Ser | Gln | Ser | Leu | Ser | Leu | Thr | Cys | Thr | Val | Ser | Gly |
| | | | | 245 | | | | | 250 | | | | | 255 | |
| Phe | Ser | Leu | Thr | Ser | Tyr | Gly | Val | His | Trp | Val | Arg | Gln | Pro | Pro | Gly |
| | | | 260 | | | | | 265 | | | | | 270 | | |
| Lys | Gly | Leu | Glu | Trp | Ile | Gly | Leu | Ile | Trp | Ser | Gly | Gly | Thr | Asp |
| | | 275 | | | | | 280 | | | | | 285 | | | |
| Tyr | Asn | Pro | Ser | Leu | Lys | Ser | Arg | Leu | Thr | Ile | Ser | Arg | Asp | Thr | Ser |
| | 290 | | | | | 295 | | | | | 300 | | | | |
| Lys | Asn | Gln | Val | Ser | Phe | Lys | Ile | Ser | Ser | Leu | Thr | Ala | Ala | Asp | Thr |
| 305 | | | | | 310 | | | | | 315 | | | | | 320 |
| Ala | Val | Tyr | Tyr | Cys | Ala | Arg | Gln | Leu | Gly | Leu | Arg | Ala | Met | Asp | Tyr |
| | | | | 325 | | | | | 330 | | | | | 335 | |
| Trp | Gly | Gln | Gly | Thr | Ser | Val | Thr | Val | Ser | Ser | Ala | Ser | Thr | Lys | Gly |
| | | | 340 | | | | | 345 | | | | | 350 | | |

Pro Ser Val Phe Pro Leu Ala Pro Cys Ser Arg Ser Thr Ser Glu Ser
        355                 360                 365

Thr Ala Ala Leu Gly Cys Leu Val Lys Asp Tyr Phe Pro Glu Pro Val
    370                 375                 380

Thr Val Ser Trp Asn Ser Gly Ala Leu Thr Ser Gly Val His Thr Phe
385                 390                 395                 400

Pro Ala Val Leu Gln Ser Ser Gly Leu Tyr Ser Leu Ser Ser Val Val
                405                 410                 415

Thr Val Pro Ser Ser Ser Leu Gly Thr Lys Thr Tyr Thr Cys Asn Val
            420                 425                 430

Asp His Lys Pro Ser Asn Thr Lys Val Asp Lys Arg Val Glu Ser Lys
        435                 440                 445

Tyr Gly Pro Pro Cys Pro Pro Cys Pro Ala Pro Glu Phe Leu Gly Gly
    450                 455                 460

Pro Ser Val Phe Leu Phe Pro Pro Lys Pro Lys Asp Thr Leu Met Ile
465                 470                 475                 480

Ser Arg Thr Pro Glu Val Thr Cys Val Val Val Asp Val Ser Gln Glu
                485                 490                 495

Asp Pro Glu Val Gln Phe Asn Trp Tyr Val Asp Gly Val Glu Val His
            500                 505                 510

Asn Ala Lys Thr Lys Pro Arg Glu Glu Gln Phe Asn Ser Thr Tyr Arg
        515                 520                 525

Val Val Ser Val Leu Thr Val Leu His Gln Asp Trp Leu Asn Gly Lys
    530                 535                 540

Glu Tyr Lys Cys Lys Val Ser Asn Lys Gly Leu Pro Ser Ser Ile Glu
545                 550                 555                 560

Lys Thr Ile Ser Lys Ala Lys Gly Gln Pro Arg Glu Pro Gln Val Tyr
                565                 570                 575

Thr Leu Pro Pro Ser Gln Glu Glu Met Thr Lys Asn Gln Val Ser Leu
            580                 585                 590

Thr Cys Leu Val Lys Gly Phe Tyr Pro Ser Asp Ile Ala Val Glu Trp
        595                 600                 605

Glu Ser Asn Gly Gln Pro Glu Asn Asn Tyr Lys Thr Thr Pro Pro Val
    610                 615                 620

Leu Asp Ser Asp Gly Ser Phe Phe Leu Tyr Ser Arg Leu Thr Val Asp
625                 630                 635                 640

Lys Ser Arg Trp Gln Glu Gly Asn Val Phe Ser Cys Ser Val Met His
                645                 650                 655

Glu Ala Leu His Asn His Tyr Thr Gln Lys Ser Leu Ser Leu Ser Leu
            660                 665                 670

Gly Lys

<210> SEQ ID NO 32
<211> LENGTH: 2022
<212> TYPE: DNA
<213> ORGANISM: Artificial
<220> FEATURE:
<223> OTHER INFORMATION: Nucleotide sequence of 609-Fab-PDL1-IgG4

<400> SEQUENCE: 32
gaggtcaagc tggtggaaag cggcggcggc ctggtgcagc ctggaggatc cctgcggctg      60
agctgcgctg cctccggctt cgctttcagc tcctatgaca tgtcctgggt gaggcaggcc     120
cctggaaaga ggctggagtg ggtggctacc atctccggag gcggaaggta cacctactac     180

```
cccgacacag tgaagggaag gttcaccatc agccgggata acgccaaaaa cagccactat    240
ctccagatga actccctgag ggccgaagat acagccgtgt atttctgtgc ctcccctac     300 ggaggctatt ttgacgtgtg gggacagggc accctggtga ccgtctcctc cgcaagtacc    360
aagggaccta gtgttttccc tcttgcacct tgctccaggt caacatcaga gtccacagct    420
gctcttggat gtctcgttaa ggactacttc ccagagccag ttaccgtatc ctggaactcc    480
ggagctttga caagcggcgt tcatacattc ccagctgtgt tgcagagttc tgggttgtac    540
agtttgagct cagtggtgac cgtgccttca tcttctttgg gcactaagac ctacacctgc    600
aacgtggatc acaagccaag caacaccaag gtggataaga gggtgggtgg aggcggttca    660
ggcggaggtg gcagcggagg tggcgggagt caggtccagc tgcagcagtc aggagggggc    720
ctggtgaagc catcacagag cctgtccctg acctgcacag tctctgggtt cagtctgact    780
tcatacggag tgcactgggt ccgacagccc cctggaaagg gactggagtg gatcggcctg    840
atttggtctg gcggggggaac agactataac cccagcctga atcccggct gaccatctct    900 agagatacca gtaagaatca agtgagcttt aaaattagct ccctgacagc cgctgacact    960
gcagtgtact attgtgcaag gcagctggga ctgcgagcta tggattactg gggacagggc    1020
acttccgtga ccgtctctag tgcaagtacc aagggaccta gtgttttccc tcttgcacct    1080
tgctccaggt caacatcaga gtccacagct gctcttggat gtctcgttaa ggactacttc    1140
ccagagccag ttaccgtatc ctggaactcc ggagctttga caagcggcgt tcatacattc    1200
ccagctgtgt tgcagagttc tgggttgtac agtttgagct cagtggtgac cgtgccttca    1260
tcttctttgg gcactaagac ctacacctgc aacgtggatc acaagccaag caacaccaag    1320
gtggataaga gggtggagtc caagtacggc ccaccatgtc ctccatgtcc agcccctgaa    1380
tttttgggcg ggccttctgt ctttctgttt cctcctaaac ctaaagatac cctgatgatc    1440
agccgcacac ccgaagtcac ttgtgtggtc gtggatgtgt ctcaggaaga tcccgaagtg    1500
cagtttaact ggtatgtcga tggcgtggaa gtgcataatg ccaaaactaa gccccgcgaa    1560
gaacagttca acagcactta tcgggtcgtg tctgtgctca cagtcctcca tcaggattgg    1620
ctgaatggga aagaatataa gtgcaaggtg agcaataagg gcctccccag cagcatcgag    1680
aagactatta gcaaagccaa agggcagcca cgggaaccc aggtgtacac tctgccccc     1740 tctcaggagg agatgactaa aaatcaggtc tctctgactt gtctggtgaa agggttttat    1800
cccagcgaca ttgccgtgga gtgggagtct aatggccagc ccgagaataa ttataagaca    1860
actccccccg tcctggactc tgacggcagc ttttttcctgt attctcggct gacagtggac    1920
aaaagtcgct ggcaggaggg caatgtcttt agttgcagtg tcatgcatga ggccctgcac    1980
aatcactata cacagaaaag cctgtctctg agtctgggca aa                       2022
```

TETRAVALENT BISPECIFIC ANTIBODY AGAINST PD-1 AND PD-L1

CROSS REFERENCE TO RELATED APPLICATIONS

This patent application is the national stage of International Application No. PCT/CN2021/088154, filed on Apr. 19, 2021, which claims the benefit and priority of International Application No. PCT/CN2020/090442, filed on May 15, 2020, the disclosures of which are incorporated by reference herein in their entirety as part of the present application.

FIELD OF THE INVENTION

The present invention relates to the field of antibodies. More particularly, the present invention discloses a tetravalent bispecific antibody against PD-1 and PD-L1.

BACKGROUND OF THE INVENTION

Human programmed cell death receptor-1 (PD-1) is a type I membrane protein of 288 amino acids and is one of the known major immune checkpoints (Blank et al, 2005, Cancer Immunotherapy, 54:307-314). PD-1 is expressed in activated T lymphocytes, and it binds to the ligands PD-L1 (programmed cell death-Ligand 1) and PD-L2 (programmed cell death-Ligand 2) to inhibit the activity of T lymphocytes and related cellular immune responses in vivo. PD-L2 is mainly expressed in macrophages and dendritic cells, while PD-L1 is widely expressed in B, T lymphocytes and peripheral cells such as microvascular epithelial cells, tissue cells of lung, liver, heart and the like. Numerous studies have shown that the interaction between PD-1 and PD-L1 is not only necessary to maintain the balance of the immune system in vivo, but also the main mechanism and cause of PD-L1 expression-positive tumor cells to evade immune surveillance. By blocking the negative regulation of cancer cells on the PD-1/PD-L1 signaling pathway and activating the immune system, T cell-related tumor-specific cellular immune responses can be promoted, thereby opening a new door for tumor treatment—tumor immunotherapy.

PD-1 (encoded by the gene Pdcd1) is a member of the immunoglobulin superfamily related to CD28 and CTLA-4. Studies have shown that PD-1 negatively regulates antigen receptor signal transduction upon engagement of its ligands (PD-L1 and/or PD-L2). At present, the structure of mouse PD-1 and the co-crystal structure of mouse PD-1 with human PD-L1 have been clarified (Zhang, X. et al., Immunity 20: 337-347 (2004); Lin et al., Proc.Natl.Acad.Sci.USA 105: 3011-6(2008)). PD-1 and similar family members are type I transmembrane glycoproteins, which contain an Ig variable (V-type) domain that is responsible for ligand binding and a cytoplasmic tail that is responsible for the binding of signal transduction molecules. The cytoplasmic tail of PD-1 contains two tyrosine-based signal transduction motifs, an ITIM (immunoreceptor tyrosine-based inhibition motif) and an ITSM (immunoreceptor tyrosine-based switch motif).

PD-1 plays an important role in tumor immune evasion mechanism. Tumor immunotherapy, which uses the body's own immune system to fight cancer, is a breakthrough in cancer treatment. However, the tumor microenvironment may protect tumor cells from effective immune damage, so how to break the tumor microenvironment becomes the focus of anti-tumor research. Existing research results have identified the role of PD-1 in the tumor microenvironment: PD-L1 is expressed in many mouse and human tumors (and may be induced by IFNγ in most PD-L1-negative tumor cell lines), and presumed to be an important target for mediating tumor immune evasion (Iwai Y. et al., Proc.Natl.Acad.Sci.U.S.A.99: 12293-12297(2002); Strome S. E. et al., Cancer Res., 63: 6501-6505(2003). Through immunohistochemical assessment of biopsies, the expression of PD-1 (on tumor infiltrating lymphocytes) and/or PD-L1 on tumor cells has been found in many primary human tumors. Such tissues include lung cancer, liver cancer, ovarian cancer, cervical cancer, skin cancer, colon cancer, glioma, bladder cancer, breast cancer, kidney cancer, esophageal cancer, gastric cancer, oral squamous cell carcinoma, urothelial cell carcinoma, and pancreatic cancer as well as tumors of head and neck, etc. Thus, blocking the interaction of PD-1/PD-L1 can improve the immune activity of tumor-specific T cells and help the immune system to clear tumor cells. Therefore, PD-1 and PD-L1 have become popular targets for development of tumor immunotherapy drugs.

Bispecific antibodies refer to antibody molecules that can specifically bind to two antigens or two epitopes at the same time. According to symmetry, bispecific antibodies can be divided into structurally symmetric and asymmetric molecules. According to the number of binding sites, bispecific antibodies can be divided into bivalent, trivalent, tetravalent and multivalent molecules. Bispecific antibodies are gradually becoming a new class of therapeutic antibodies that may be used to treat various inflammatory diseases, cancers and other diseases. Although a large number of new bispecific antibody structural forms have been reported recently, the main technical difficulty in producing bispecific antibodies lies in obtaining the correct paired molecules. The current forms of bispecific antibodies all have mismatch problems, so one or more by-products or aggregates caused by mismatches will be produced, thereby affecting the yield, purity and physical and chemical stability of the bispecific antibodies of interest, and further affecting the safety and efficiency of the bispecific antibodies in vivo.

SUMMARY OF THE INVENTION

The present invention provides an antibody that binds to human PD-L1, and a tetravalent bispecific antibody against PD-1 and PD-L1 constructed based on the antibody that binds to human PD-L1.

Therefore, the first object of the present invention is to provide an antibody that binds to human PD-L1 or an antigen-binding fragment thereof.

The second object of the present invention is to provide an isolated nucleotide encoding the antibody that binds to human PD-L1 or the antigen-binding fragment thereof.

The third object of the present invention is to provide an expression vector comprising the nucleotide.

The fourth object of the present invention is to provide a host cell comprising the expression vector.

The fifth object of the present invention is to provide a method of preparing the antibody that binds to human PD-L1 or the antigen-binding fragment thereof.

The sixth object of the present invention is to provide a pharmaceutical composition comprising the antibody that binds to human PD-L1 or the antigen-binding fragment thereof.

The seventh object of the present invention is to provide the use of the antibody that binds to human PD-L1 or the antigen-binding fragment thereof or the pharmaceutical composition in the preparation of a medicine for the treatment of PD-L1 overexpression diseases.

The eighth object of the present invention is to provide a method of treating PD-L1 overexpression diseases with the antibody that binds to human PD-L1 or the antigen-binding fragment thereof or the pharmaceutical composition.

The ninth object of the present invention is to provide a tetravalent bispecific antibody against PD-1 and PD-L1.

The tenth object of the present invention is to provide an isolated nucleotide encoding the tetravalent bispecific antibody.

The eleventh object of the present invention is to provide an expression vector comprising the nucleotide.

The twelfth object of the present invention is to provide a host cell comprising the expression vector.

The thirteenth object of the present invention is to provide a method of preparing the tetravalent bispecific antibody.

The fourteenth object of the present invention is to provide a pharmaceutical composition comprising the tetravalent bispecific antibody.

The fifteenth object of the present invention is to provide the use of the tetravalent bispecific antibody or the pharmaceutical composition in the preparation of a medicine for the treatment of cancer.

The sixteenth object of the present invention is to provide a method of treating cancer with the tetravalent bispecific antibody or the pharmaceutical composition.

In order to achieve the above objects, the present invention provides the following technical solutions:

The first aspect of the present invention provides an antibody that binds to human PD-L1 or the antigen-binding fragment thereof, comprising:
  (a) heavy chain complementarity determining regions H-CDR1, H-CDR2, H-CDR3, the H-CDR1 having an amino acid sequence as shown in SEQ ID NO: 17, the H-CDR2 having an amino acid sequence as shown in SEQ ID NO: 18, and the H-CDR3 having an amino acid sequence as shown in SEQ ID NO:19, and
  (b) light chain complementarity determining regions L-CDR1, L-CDR2, L-CDR3, the L-CDR1 having an amino acid sequence as shown in SEQ ID NO: 20, the L-CDR2 having an amino acid sequence as shown in SEQ ID NO: 21, and the L-CDR3 having an amino acid sequence as shown in SEQ ID NO: 22.

According to the present invention, the antibody is a monoclonal antibody or a polyclonal antibody.

According to the present invention, the antibody is a murine antibody, a chimeric antibody, or a humanized antibody.

According to the present invention, the antigen-binding fragment comprises a Fab fragment, a F(ab')2 fragment, a Fv fragment or a single chain antibody.

According to the present invention, the antibody that binds to human PD-L1 or the antigen-binding fragment thereof comprises a heavy chain variable region having an amino acid sequence as shown in SEQ ID NO: 9, and a light chain variable region having an amino acid sequence as shown in SEQ ID NO: 10.

According to the present invention, the antibody that binds to human PD-L1 or the antigen-binding fragment thereof comprises a heavy chain having an amino acid sequence as shown in SEQ ID NO: 13, and a light chain having an amino acid sequence as shown in SEQ ID NO: 15.

The second aspect of the present invention provides an isolated nucleotide, which encodes the antibody that binds to human PD-L1 or the antigen-binding fragment thereof as described above.

According to the present invention, the nucleotide sequence encoding the heavy chain of the antibody that binds to human PD-L1 or the antigen-binding fragment thereof is shown in SEQ ID NO: 14, and the nucleotide sequence encoding the light chain is shown in SEQ ID NO: 16.

The third aspect of the present invention provides an expression vector, which comprises the nucleotides as described above.

The fourth aspect of the present invention provides a host cell, which comprises the expression vector as described above.

The fifth aspect of the present invention provides a method of preparing the antibody that binds to human PD-L1 or the antigen-binding fragment thereof, which comprises the following steps:
  a) culturing the host cell as described above under expression conditions, to express the antibody that binds to human PD-L1 or the antigen-binding fragment thereof;
  b) isolating and purifying the antibody that binds to human PD-L1 or the antigen-binding fragment thereof of step a).

The sixth aspect of the present invention provides a pharmaceutical composition, which comprises the antibody that binds to human PD-L1 or the antigen-binding fragment thereof as described above and a pharmaceutically acceptable carrier.

The seventh aspect of the present invention provides the use of the antibody that binds to human PD-L1 or the antigen-binding fragment thereof, or of the pharmaceutical composition as described above, in the preparation of a medicine for the treatment of PD-L1 overexpression diseases.

According to the present invention, the PD-L1 overexpression disease is cancer. Preferably, the cancer is selected from the group consisting of melanoma, kidney cancer, prostate cancer, pancreatic cancer, breast cancer, colon cancer, lung cancer, esophageal cancer, head and neck squamous cell carcinoma, liver cancer, ovarian cancer, cervical cancer, thyroid cancer, glioblastoma, glioma, leukemia, lymphoma and other neoplastic malignant diseases, etc.

The eighth aspect of the present invention provides a method of treating PD-L1 overexpression diseases, which comprises administering the antibody that binds to human PD-L1 or the antigen-binding fragment thereof or the pharmaceutical composition as described above to a subject in need.

According to the present invention, the PD-L1 overexpression disease is cancer. Preferably, the cancer is selected from the group consisting of melanoma, kidney cancer, prostate cancer, pancreatic cancer, breast cancer, colon cancer, lung cancer, esophageal cancer, head and neck squamous cell carcinoma, liver cancer, ovarian cancer, cervical cancer, thyroid cancer, glioblastoma, glioma, leukemia, lymphoma and other neoplastic malignant diseases, etc.

The ninth aspect of the present invention provides a tetravalent bispecific antibody against PD-1 and PD-L1, comprising two polypeptide chains and four common light chains, wherein the polypeptide chains have an amino acid sequence as shown in SEQ ID NO: 29 or SEQ ID NO: 31, and the common light chains have the amino acid sequence as shown in SEQ ID NO: 15.

The tenth aspect of the present invention provides an isolated nucleotide, which encodes the tetravalent bispecific antibody.

According to a preferred embodiment of the present invention, the nucleotide encodes the polypeptide chains and the common light chains, wherein the nucleotide sequence encoding the polypeptide chains is as shown in SEQ ID NO: 30 or SEQ ID NO: 32, the nucleotide sequence encoding the common light chains is as shown in SEQ ID NO:16.

The eleventh aspect of the present invention provides an expression vector, which comprises the nucleotide as described above.

The twelfth aspect of the present invention provides a host cell, which comprises the expression vector as described above.

The thirteenth aspect of the present invention provides a method of preparing the tetravalent bispecific antibody, which comprises the following steps:
 a) culturing the host cell as described above under expression conditions, to express the tetravalent bispecific antibody;
 b) isolating and purifying the tetravalent bispecific antibody of step a).

The fourteenth aspect of the present invention provides a pharmaceutical composition, which comprises the tetravalent bispecific antibody as described above and a pharmaceutically acceptable carrier.

The fifteenth aspect of the present invention provides the use of the tetravalent bispecific antibody or the pharmaceutical composition as described above in the preparation of a medicine for the treatment of cancer.

According to the present invention, the cancer is selected from the group consisting of melanoma, kidney cancer, prostate cancer, pancreatic cancer, breast cancer, colon cancer, lung cancer, esophageal cancer, head and neck squamous cell carcinoma, liver cancer, ovarian cancer, cervical cancer, thyroid cancer, glioblastoma, glioma, leukemia, lymphoma and other neoplastic malignant diseases, etc.

The sixteenth aspect of the present invention provides a method of treating cancers, which comprises administering the tetravalent bispecific antibody or the pharmaceutical composition as described above to a subject in need.

According to the present invention, the cancer is selected from the group consisting of melanoma, kidney cancer, prostate cancer, pancreatic cancer, breast cancer, colon cancer, lung cancer, esophageal cancer, head and neck squamous cell carcinoma, liver cancer, ovarian cancer, cervical cancer, thyroid cancer, glioblastoma, glioma, leukemia, lymphoma and other neoplastic malignant diseases, etc.

Benefit Effect:

The present invention provides an antibody that binds to human PD-L1, and a tetravalent bispecific antibody against PD-1 and PD-L1 constructed based on the antibody that binds to human PD-L1. The tetravalent bispecific antibody of the present invention requires no Fc modification, has no mismatch problems, and the preparation method thereof is simple. Its biological activities and physical and chemical properties are similar with or even better than those of the monoclonal antibodies.

DETAILED DESCRIPTION OF THE INVENTION

Figure 1:
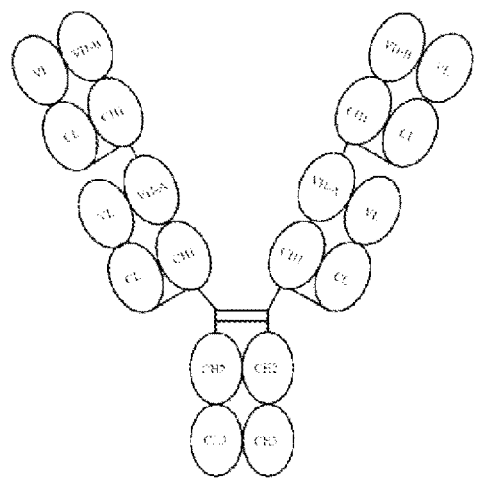
FIG. 1 is a schematic diagram of the structure of the bispecific antibody of the present invention, where VH-A represents the heavy chain variable region of Anti-PDL1 or 609, VH-B represents the heavy chain variable region of 609 or Anti-PDL1, and VL represents the light chain variable region of the common light chains, CHL CH2, and CH3 are the three domains of the heavy chain constant region, CL is the light chain constant region of the common light chains, and the line between the two heavy chains represents the disulfide bond, the line between the heavy chain and the light chain also represents the disulfide bond, the line between the CH1 near the N-terminus of the polypeptide chain and the VH-A represents the artificially designed linker, and the line between the CH1 near the C-terminus of the polypeptide chain and the CH2 represents the natural linker and hinge region of the antibody (if the heavy chain is human IgG4 subtype, the hinge region contains the S228P mutation, according to the EU numbering).

The sequence information involved in the present invention is summarized in Table 1.

TABLE 1

Sequence information of the antibodies of the present invention

| SEQ ID NO: | Sequence name |
|---|---|
| 1 | Amino acid sequence of the heavy chain complementarity determining region H-CDR1 of murine M8 antibody |
| 2 | Amino acid sequence of the heavy chain complementarity determining region H-CDR2 of murine M8 antibody |
| 3 | Amino acid sequence of the heavy chain complementarity determining region H-CDR3 of murine M8 antibody |
| 4 | Amino acid sequence of the light chain complementarity determining region L-CDR1 of murine M8 antibody |

TABLE 1-continued

Sequence information of the antibodies of the present invention

| SEQ ID NO: | Sequence name |
|---|---|
| 5 | Amino acid sequence of the light chain complementarity determining region L-CDR2 of murine M8 antibody |
| 6 | Amino acid sequence of the light chain complementarity determining region L-CDR3 of murine M8 antibody |
| 7 | the fourth framework region of heavy chain (WGQGTSVTVSS) |
| 8 | the fourth framework region of light chain (FGAGTKLEIK) |
| 9 | Amino acid sequence of the heavy chain variable region of Anti-PDL1 |
| 10 | Amino acid sequence of the light chain variable region of Anti-PDL1 |
| 11 | Amino acid sequence of the heavy chain constant region of human IgG1 |
| 12 | Amino acid sequence of human Kappa light chain constant region |
| 13 | Amino acid sequence of heavy chain of Anti-PDL1 |
| 14 | Nucleotide sequence of heavy chain of Anti-PDL1 |
| 15 | Amino acid sequence of light chain of Anti-PDL1 |
| 16 | Nucleotide sequence of light chain of Anti-PDL1 |
| 17 | Amino acid sequence of heavy chain complementarity determining region H-CDR1 of Anti-PDL1 |
| 18 | Amino acid sequence of heavy chain complementarity determining region H-CDR2 of Anti-PDL1 |
| 19 | Amino acid sequence of heavy chain complementarity determining region H-CDR3 of Anti-PDL1 |
| 20 | Amino acid sequence of light chain complementarity determining region L-CDR1 of Anti-PDL1 |
| 21 | Amino acid sequence of light chain complementarity determining region L-CDR2 of Anti-PDL1 |
| 22 | Amino acid sequence of light chain complementarity determining region L-CDR3 of Anti-PDL1 |
| 23 | Amino acid sequence of heavy chain variable region of Atezolizumab |
| 24 | Amino acid sequence of light chain variable region of Atezolizumab |
| 25 | Amino acid sequence of heavy chain variable region of mAb1-25-Hu (609) |
| 26 | Amino acid sequence of light chain variable region of mAb1-25-Hu (609) |
| 27 | Amino acid sequence of heavy chain constant region of IgG4 (S228P) |
| 28 | Linker (GGGGSGGGGSGGGGS) |
| 29 | Amino acid sequence of PDL1-Fab-609-IgG4 |
| 30 | Nucleotide sequence of PDL1-Fab-609-IgG4 |
| 31 | Amino acid sequence of 609-Fab-PDL1-IgG4 |
| 32 | Nucleotide sequence of 609-Fab-PDL1-IgG4 |

In the present invention, the terms "antibody (abbreviated as Ab)" and "immunoglobulin G (abbreviated as IgG)" are heterotetrameric glycoproteins of about 150,000 daltons with identical structural characteristics, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable region (VH) followed by constant regions. The heavy chain constant region is composed of three structural domains, CH1, CH2, and CH3. Each light chain has a variable region (VL) at one end and a constant region at its other end, the light chain constant region includes a domain CL; the constant region of the light chain is paired with the CH1 domain of the constant region the heavy chain, and the light chain variable region is paired with the variable region of the heavy chain. The constant regions are not involved directly in binding an antibody to an antigen, but they exhibit various effector functions, such as participation in antibody-dependent cell-mediated cytotoxicity (ADCC). The heavy chain constant region includes IgG1, IgG2, IgG3, IgG4 subtypes; the light chain constant region includes κ (Kappa) or 2 (Lambda). The heavy chain and light chain of the antibody are covalently linked together by the disulfide bond between the CH1 domain of the heavy chain and the CL domain of the light chain, and the two heavy chains of the antibody are covalently linked together by inter-polypeptide disulfide bonds formed between the hinge regions.

The antibody of the present invention comprises monoclonal antibodies, polyclonal antibodies, multispecific antibodies formed from at least two antibodies (such as bispecific antibodies), antigen-binding fragments of antibodies, etc. The antibody of the present invention comprises murine antibodies, chimeric antibodies, humanized antibodies, etc.

In the present invention, the term "bispecific antibody (BsAb)" refers to an antibody molecule that can specifically bind two antigens (targets) or two epitopes at the same time.

In the present invention, the term "monoclonal antibody (mAb)" refers to an antibody obtained from a population of substantially homogeneous antibodies, that is, the individual antibodies contained in the population are the same, except for a few possible naturally occurring mutations. Monoclonal antibodies target a single antigen site with high specificity. Moreover, unlike conventional polyclonal antibody preparations (usually a mixture having different antibodies directed against different antigen determinants), each monoclonal antibody is directed against a single determinant on the antigen. Besides their specificity, the benefit of monoclonal antibodies is that they can be synthesized by hybridoma culture and are not contaminated by other immunoglobulins. The modifier "monoclonal" indicates the characteristics of an antibody, which is obtained from a substantially uniform antibody population, and should not be interpreted as requiring any special method to produce the antibody.

In the present invention, the term "murine antibody" refers to an antibody derived from rats or mice, preferably mice. The murine antibody of the present invention is obtained by immunizing mice with the extracellular domain of human PD-L1 as an antigen and screening hybridoma cells.

In the present invention, the term "chimeric antibody" refers to an antibody that comprises heavy and light chain variable region sequences from one species and constant region sequences from another species, such as an antibody having mouse heavy and light chain variable regions linked to human constant region.

In the present invention, the term "humanized antibody" means that the CDRs are derived from a non-human (preferably, mouse) antibody, while the remaining parts (including framework regions and constant regions) are derived from human antibody. In addition, framework region residues may be altered to preserve the binding affinity.

In the present invention, the term "antigen-binding fragment" refers to a fragment of an antibody capable of specifically binding to an epitope of human PD-L1. Examples of the antigen-binding fragments of the present invention include Fab fragments, F(ab')2 fragments, Fv fragments, and single chain antibodies (scFv). The Fab fragment is composed of the domains which are the VH and CH1 of the heavy chain of the antibody, and the VL and CL of the light chain of the antibody. The F(ab')2 fragment is a fragment produced by digesting the antibody with pepsin. The Fv fragment is composed of dimers in which the heavy chain variable region and the light chain variable region of the antibody are closely and non-covalently related. The single-chain antibody (scFv) is an antibody in which the heavy chain variable region and the light chain variable region of the antibody are linked by a short peptide (linker) of 15-20 amino acids.

In the present invention, the term "Fc" is a fragment crystallizable (Fc), which is composed of the CH2 and CH3 domains of an antibody. The Fc segment has no antigen binding activity and is the site where the antibody interacts with effector molecules or cells.

In the present invention, the term "variable" refers to the fact that certain portions of the variable regions differ extensively in sequence among antibodies and are responsible for the binding specificity of each particular antibody for its particular antigen. However, the variability is not evenly distributed through the variable regions of antibodies. It is concentrated in three segments called complementarity determining regions (CDRs) or hypervariable regions both in the light chain variable regions and the heavy chain variable regions. The more highly conserved portions of the variable regions are called the framework regions (FR). The variable regions of native heavy and light chains each comprise four FR regions, largely adopting a β-sheet configuration, connected by three CDRs, which form loops connecting, and in some cases forming part of the β-sheet structure. The CDRs in each chain are held together in close proximity by the FR regions and, with the CDRs from the other chain, contribute to the formation of the antigen binding site of antibodies (see Kabat et al., NIH Publ.No. 91-3242, Volume I, pages 647-669 (1991)).

In the present invention, the terms "anti-/against" and "binding" refer to a non-random binding reaction between two molecules, such as the reaction between an antibody and the antigen it is directed against. Generally, the antibody binds to the antigen with an equilibrium dissociation constant (KD) of less than about $10^{-7}$ M, for example, less than about $10^{-8}$ M, $10^{-9}$ M, $10^{-19}$ M, $10^{-11}$ M or less. In the present invention, the term "KD" refers to the equilibrium dissociation constant of a specific antibody-antigen interaction, which is used to describe the binding affinity between the antibody and the antigen. The smaller the equilibrium dissociation constant is, the tighter the antibody-antigen binding is, and the higher the affinity between the antibody and the antigen is. For example, surface plasmon resonance (abbreviated as SPR) is used to measure the binding affinity of antibody to antigen in BIACORE instrument or ELISA is used to measure the relative binding affinity of antibody to antigen.

In the present invention, the term "valency" refers to the presence of a specified number of antigen binding sites in an antibody molecule. Preferably, the bispecific antibody of the present invention has four antigen binding sites and is tetravalent. In the present invention, the antigen binding site includes a heavy chain variable region (VH) and a light chain variable region (VL).

In the present invention, the term "epitope" refers to a polypeptide determinant that specifically binds to an antibody. The epitope of the present invention is a region of an antigen that is bound by an antibody.

In the present invention, the term "common light chain" refers to a light chain comprising the same light chain variable region and light chain constant region, which can pair with the heavy chain of a first antibody that binds to a first antigen to form a binding site that specifically binds to the first antigen, and can also pair with the heavy chain of a second antibody that binds to a second antigen to form a binding site that specifically binds to the second antigen. Further, the light chain variable region of the common light chain and the heavy chain variable region of the first antibody form the first antigen binding site, and the light chain variable region of the common light chain and the heavy chain variable region of the second antibody form the second antigen binding site.

In the present invention, the term "expression vector" may be pTT5, pSECtag series, pCGS3 series, pCDNA series vectors, as well as other vectors used in mammalian expression systems, etc. The expression vector comprises a fusion DNA sequence connected with appropriate transcription and translation regulatory sequences.

In the present invention, the term "host cell" refers to a cell suitable for expressing the expression vector as described above, which may be a eukaryotic cell, for example, mammalian or insect host cell culture system may be used to express the fusion protein of the present invention, CHO (Chinese hamster Ovary), HEK293, COS, BHK, as well as derived cells of the above-mentioned cells are applicable to the present invention.

In the present invention, the term "pharmaceutical composition" means that the antibody or antigen-binding fragment thereof that binds to human PD-L1 or the tetravalent bispecific antibody of the present invention can be combined with a pharmaceutically acceptable carrier to form a pharmaceutical preparation composition, so as to exert a therapeutic effect more stably. These preparations can ensure the conformational integrity of the amino acid core sequences of the antibody or antigen-binding fragment thereof that binds to human PD-L1 disclosed in the present invention, and meanwhile, protect the multifunctional groups of the protein from degradation (including but not limited to aggregation, deamination or oxidation).

The protein expression and purification methods used in the following examples are described as follows: the target genes are constructed into the expression vector pcDNA4, and the constructed expression vectors or combination of expression vectors are transferred into FreeStyle™ 293-F cells (hereinafter referred to as HEK293F, purchased from Thermo Fisher Scientific) using PEI (Polyethylenimine), to express an antibody or recombinant protein. HEK293F cells are cultured in Free Style 293 Expression Medium (purchased from Thermo Fisher Scientific) for 5 days and the cell supernatant are collected, and then the antibody or recombinant protein are purified by ProteinA affinity chromatography or nickel affinity chromatography.

The mixed lymphocyte reaction (MLR) method used in the following examples is described as follows: Peripheral blood mononuclear cells (PBMC) are separated from human blood using Histopaque (purchased from Sigma), and then the monocytes in PBMC are separated by adherence method, and then the monocytes are induced with IL-4 (25 ng/ml) and GM-CSF (25 ng/ml) to differentiate into dendritic cells. Seven days later, the above-induced dendritic cells are digested and collected. PBMCs are separated from the blood of other donors by the above method, and then $CD4^+$ T cells are separated from PBMCs with MACS magnet and CD4 MicroBeads (purchased from Miltenyibiotec). The induced dendritic cells ($10^4$/well) and the isolated $CD4^+$ T cells ($10^5$/well) are mixed in proportion and then inoculated into a 96-well plate, 150 µl per well; a few hours later, 50 µl of serially diluted antibody is added into the above 96-well plate; the 96-well plate is incubated in a 37° C. cell incubator for 3 days. During the above experiment, AIM-V medium (purchased from Thermo Fisher Scientific) is used to culture the cells. Then, the secretion of IL-2 and IFN-γ is detected in accordance with standard operating procedures. IL-2 and IFN-γ are detected using double-antibody sandwich ELISA (related paired antibodies are purchased from BD Biosciences). OD450 values are read with a microplate reader (SpectraMax 190). Graphing is performed by GraphPad Prism6 and EC50 values are calculated.

The methods for detecting physical and chemical properties used in the following examples are described as follows:

HPLC-SEC

Antibodies are high molecular weight proteins with highly complex secondary and tertiary structures. Due to changes such as post-translational modification, aggregation, and degradation, antibodies are heterogeneous in their biochemical and biophysical properties. Variants, aggregates, and degraded fragments are commonly observed when bispecific antibodies are analyzed by separation techniques, and their presence may compromise safety and effectiveness. Aggregates, degraded fragments and incompletely assembled molecules are prone to appear during production and storage of an antibody. In the present invention, high-performance liquid chromatography—size exclusion chromatography (HPLC-SEC) is used to detect the content of the above impurities in a sample. The molecular weight of the aggregate is larger than that of the monomer, so the retention time of the corresponding peak is shorter; the molecular weight of the degraded fragment or the incompletely assembled molecule is smaller than that of the monomer, so the retention time of the corresponding peak is longer. Chromatograph used for HPLC-SEC: Dionex Ultimate 3000; the method for the preparation of mobile phase is as follows: an appropriate amount of 20 mM sodium dihydrogen phosphate mother liquor is adjusted with 20 mM disodium hydrogen phosphate to a pH of 6.8±0.1; injection amount: 20 µg; chromatograph column: TSK G3000SWXL, specification: 7.8×300 mm 5 µm; flow rate: 0.5 ml/min, elution time: 30 mM; column temperature: 25° C., sample room temperature: 10° C.; detection wavelength: 214 nm.

HPLC-IEC

Many post-translational modifications (such as N-glycosylation, C-terminal lysine residue modification, N-terminal glutamine or glutamate cyclization, asparagine deamidation, aspartic acid isomerization, amino acid residue oxidation, etc.) will directly or indirectly change the surface charge of the antibody, leading to the generation of charge heterogeneity. The charge variants can be separated and analyzed based on the charge. Commonly used analysis methods include cation exchange chromatography (CEX) and anion exchange chromatography (AEX). When analyzed by a chromatography-based method, acidic species and basic species are defined based on their retention time relative to the main peak. The acidic species are the variants that eluted earlier than the main peak of CEX or later than the main peak of AEX, while the basic species are the variants that eluted later than the main peak of CEX or earlier than the main peak of AEX. The peaks corresponding to the acidic species and the basic species are called acidic peaks and basic peaks, respectively. Charge variants are easily generated during the production and storage of antibodies. Here, high-performance liquid chromatography-ion exchange chromatography (HPLC-IEC) is used to analyze the charge heterogeneity of the samples. Chromatograph used in HPLC-IEC: Dionex Ultimate 3000; mobile phase A: 20 mM PB pH 6.3, mobile phase B: 20 mM PB+200 mM NaCl pH 6.3, the mixing ratio of the two mobile phases changes with time according to the preset program, flow rate 1.0 ml/min; chromatographic column: Thermo Propac™ WCX-10; column temperature: 30° C., sample room temperature: 10° C.; injection amount: 20 µg; detection wavelength: 214 nm.

CE-SDS

In the present invention, CE-SDS (Capillary Electrophoresis-Sodium Dodecyl Sulfate) is used to analyze the content of degraded fragments or incompletely assembled molecules in the sample. CE is divided into two types: non-reduced and reduced; for the former, when the sample is denatured, the reducing agent DTT is not needed to destroy the disulfide bond in the molecule; for the latter, when the sample is denatured, the reducing agent DTT is needed to destroy the disulfide bond in the molecule. Non-reduced and reduced CE-SDS are denoted as NR-CE-SDS and R-CE-SDS, respectively. The capillary electrophoresis instrument used is ProteomeLab™ PA800 plus (Beckman Coulter), equipped with a UV 214 nm detector, capillary model: Bare Fused-Silica Capillary, specification: 30.7 cm×50 µm, effective length: 20.5 cm; other related reagents: purchased from Beckman Coulter. The key parameters of the instrument are set as follows: temperature of capillary and sample chamber: 20±2° C., separation voltage: 15 kV.

DSC

Differential Scanning calorimeter (DSC) reflects the thermal stability of the sample mainly by detecting the heat change in biomolecules in a controlled heating or cooling process. By heating, the unfolding of the protein sample will absorb heat, and the supplementary energy required to eliminate the temperature difference in the sample pool will be recorded by the device. These heat changes will form a peak shape in the spectrum. The peak top temperature corresponding to the unfolding of the protein sample is taken as the melting temperature Tm. Tm is an important indicator of protein thermal stability. The higher the Tm is, the better the stability of the protein is.

Molecular Weight Detection

The antibody is deglycosylated by treating with PNGase F and endoglycosidase F2. UPLC-XEVO G2 Q-TOF liquid chromatography-mass spectrometry system (Waters) is used for the analysis and identification of molecular weight of the sample. Mobile phase A is HPLC-grade water containing 0.1% trifluoroacetic acid (TFA). Mobile phase B is acetonitrile containing 0.1% TFA. In the method of detecting the complete molecular weight, the chromatographic column used is Mass PREPTM Micro Desalting Column (specification 2.1×5 mm). The key parameters are set as follows: column temperature: 80° C.; flow rate of mobile phase: 0.2 mL/min; mobile phase gradient: mobile phase B rises from 5% to 90% within 1.5 min; ESI source temperature: 130° C. BiopharmaLynx v1.2 (Waters) is used to control the liquid chromatography-mass spectrometry system and collect data, and the mass spectrum signals are deconvoluted with BiopharmaLynx v1.2.

The following examples are used to further illustrate the present invention and should not be construed as limiting the present invention. The examples do not include a detailed description of traditional methods, such as those methods of constructing expression vectors and preparing plasmids, methods of inserting genes encoding proteins into such vectors and plasmids, or methods of transfecting plasmids into host cells. Such methods are well known to those of ordinary skill in the art, and are described in many publications, including Sambrook, J., Fritsch, E. F. and Maniais, T. (1989) Molecular Cloning: A Laboratory Manual, 2nd edition, Cold spring Harbor Laboratory Press.

Example 1

Preparation of Humanized Anti-Human PD-L1 Antibody

Example 1.1

Preparation of Recombinant Proteins PD-1 and PD-L1

The source of genes encoding the extracellular regions of PD-1 and PD-L1 was described in WO2018/137576A1. Using gene recombination technology, the ends of the extracellular region coding genes of PD-1 and PD-L1 were connected to the polyhistidine coding sequence, respectively, and then the recombinant genes were cloned into the pcDNA4 expression vector, and the recombinant proteins were expressed and purified, respectively. The obtained recombinant proteins were named PD1-His and PD-L1-His, respectively. Using gene recombination technology, the ends of the extracellular region coding genes of PD-1 and PD-L1 were connected to the Fc segment coding sequence of human IgG1, respectively, and then the recombinant genes were cloned into the pcDNA4 expression vector, and the recombinant proteins were expressed and purified, respectively. The obtained recombinant proteins were named PD1-ECD-hFc and PD-L1-ECD-hFc, respectively.

Example 1.2

Preparation of Murine Anti-Human PD-L1 Monoclonal Antibody

The above PD-L1-ECD-hFc was used as an antigen to immunize Balb/c mice (purchased from Shanghai Lingchang Biotechnology Co., Ltd.). The methods of immunizing mice, detecting titer and screening hybridoma clones are described in Example 2 of WO2018/137576A1. The method of screening positive clones of hybridomas by ELISA is as follows: An ELISA plate was coated with the above PD-L1-His with a coating concentration of 10 ng/well, and blocked with PBST ($KH_2PO_4$ 0.2 g, $Na_2HPO_4·12H_2O$ 2.9 g, NaCl 8.0 g, KCl 0.2 g, Tween-20 0.5 ml, added with pure water to 1L) containing 1% bovine serum albumin (BSA). The antibody to be tested was serially diluted, and then transferred to the above plate coated with the recombinant protein, incubated at room temperature for half an hour and then the plate was washed; an appropriately diluted HRP (Horseradish Peroxidase)-labeled goat anti-mouse antibody (Fc-Specific) (purchased from Sigma) was added, incubated at room temperature for half an hour and then the plate was washed; 100 µl of chromogenic solution (chromogenic substrate solution A: sodium acetate. trihydrate 13.6 g, citric acid. monohydrate 1.6 g, 30% hydrogen peroxide 0.3 ml, pure water 500 ml; chromogenic substrate solution B: disodium ethylenediaminetetraacetic acid 0.2 g, citric acid. monohydrate 0.95 g, glycerol 50 ml, 0.15 g TMB dissolved in 3 ml DMSO, pure water 500 ml; A and B mixed in equal volume before use) with TMB (3,3',5,5'-Tetramethylbenzidine) as a substrate was added to each well, incubated at room temperature for 1-5 min; 50 µl of stop solution (2M $H_2SO_4$) was added to stop the reaction. OD450 values were read with a microplate reader (SpectraMax 190).

The positive hybridoma clones were selected for expansion in a 24-well plate and subcloned by limiting dilution method. A monoclonal hybridoma cell line stably expressing the target antibody was obtained by the above-mentioned method, and these clones were amplified. The above hybridoma cell line was cultured in serum-free medium Hybridoma-SFM (purchased from Thermo Fisher Scientific) for 7 days, and then the murine anti-human PD-L1 monoclonal antibody was purified from the culture supernatant by Protein A/G affinity chromatography. After purification, several murine monoclonal antibodies that can bind to human PD-L1 were obtained. The relative affinity of the murine monoclonal antibodies to human PD-L1 was evaluated by ELISA. Finally, the clone M8 with the highest relative affinity was selected for further development.

Example 1.3

Sequence Determination and Humanization of Murine anti-PD-L1 Monoclonal Antibody Step 1: Determination of the Variable Region Sequence of Murine Anti-Human PD-L1 Monoclonal Antibody Total RNAs were extracted from the M8 hybridoma monoclonal cell line using Trizol, and mRNAs were reverse transcribed into cDNAs using a reverse transcription kit. By the primer combination reported in the literature (Antibody Engineering, Volume 1, Edited by Roland Kontermann and Stefan Dtibel; the sequences of the primer combination from page 323), the genes of light chain variable region and heavy chain variable region of M8 were amplified by PCR, and then the PCR products were cloned into the pMD18-T vector, and the variable region genes were sequenced and analyzed.

The amino acid sequences of the light chain variable region and the heavy chain variable region of the antibody M8 were analyzed, and the complementarity-determining regions and frame regions of the antibody M8 were determined according to Kabat rule. The amino acid sequences of the heavy chain CDRs of the antibody M8 are: H-CDR1: SYGVH (SEQ ID NO: 1), H-CDR2: LIWSGGGTDYNAAFIS (SEQ ID NO: 2) and H-CDR3: QLGLRAMDY (SEQ ID NO: 3), the amino acid sequences of CDRs of the light chain are: L-CDR1: RASQSIGTTIH (SEQ ID NO: 4), L-CDR2: YASESVS (SEQ ID NO: 5) and L-CDR3: QQSNSWPLT (SEQ ID NO: 6).

Step 2: Humanization of Murine Anti-Human PD-L1 Monoclonal Antibody

The homology comparison of the heavy chain variable region of the murine antibody M8 with the human IgG germline sequence was performed at https://www.ncbi.nlm nih.gov/igblast/. Selecting IGHV4-59*01 as the heavy chain CDR grafting template, the heavy chain CDRs of the murine antibody M8 were transplanted into the framework regions of IGHV4-59*01, and WGQGTSVTVSS (SEQ ID NO: 7) was added following the H-CDR3 as the fourth framework region, to obtain a CDR-grafted heavy chain variable region sequence. Similarly, the homology comparison of the light chain variable region of the murine antibody M8 with the human IgG germline sequence was performed. Selecting IGKV6-21*01 as the light chain CDR grafting template, the light chain CDRs of the murine antibody M8 were transplanted into the framework regions of IGKV6-21*01, and FGAGTKLEIK (SEQ ID NO: 8) was added following the L-CDR3 as the fourth framework region, to obtain a CDR-grafted light chain variable region sequence. On the basis of the CDR-grafted variable regions, some amino acid sites were subjected to mutation. When mutation was performed, the amino acid sequence was numbered by Kabat rule and the position of each site was indicated by Kabat numbering.

Preferably, for the CDR-grafted heavy chain variable region, according to Kabat numbering, E at position 6 was mutated to Q, P at position 9 was mutated to G, E at position 16 was mutated to Q, T at position 17 was mutated to S, G at position 27 was mutated to F, I at position 29 was mutated to L, I at position 37 was mutated to V, A at position 61 was mutated to P, A at position 62 was mutated to S, F at position 63 was mutated to L, I at position 64 was mutated to K, V at position 67 was mutated to L, V at position 71 was mutated to R, F at position 78 was mutated to V, L at position 80 was mutated to F, L at position 82 was mutated to I, V at position 82C was mutated to L. For the CDR-grafted light chain variable region, Q at position 11 was mutated to L, E at position 53 was mutated to Q, V at position 55 was mutated to F, and L at position 78 was mutated to V.

The above heavy chain variable region and light chain variable region with mutation sites were defined as humanized heavy chain variable region and light chain variable region (SEQ ID NOs: 9 and 10), respectively. The DNAs encoding the humanized heavy chain and light chain variable regions were synthesized by Shanghai Sango Biotech Co., Ltd. The synthesized humanized heavy chain variable region was connected to the human IgG1 heavy chain constant region (SEQ ID NO: 11) to obtain a full-length humanized heavy chain gene, named Anti-PDL1-HC (SEQ ID NOs: 13 and 14). The humanized light chain variable region was connected to the human Kappa chain constant region (SEQ ID NO: 12) to obtain a full-length humanized light chain gene, named Anti-PDL1-LC (SEQ ID NOs: 15 and 16). The Anti-PDL1-HC and Anti-PDL1-LC genes were constructed into the pcDNA4 expression vector, respectively, and the resulting heavy and light chain expression vectors were transferred together into HEK293F cells by PEI transfection method to express the antibody, and the antibody was purified using Protein A affinity chromatography. The obtained antibody was named Anti-PDL1.

The final Anti-PDL1 antibody comprises the heavy chain CDRs having the amino acid sequences: H-CDR1: SYGVH (SEQ ID NO: 17), H-CDR2: LIWSGGGTDYNPSLKS (SEQ ID NO: 18) and H-CDR3: QLGLRAMDY (SEQ ID NO: 19); the light chain CDRs having the amino acid sequences: L-CDR1: RASQSIGTTIH (SEQ ID NO: 20), L-CDR2: YASQSFS (SEQ ID NO: 21) and L-CDR3: QQSNSWPLT (SEQ ID NO: 22).

Example 1.4

Preparation of Control Antibody Atezolizumab-IgG1

The sequences of heavy chain variable region and light chain variable region of the positive control antibody Atezolizumab were obtained from WHO Drug Information, Vol. 29, No. 3, 2015 (SEQ ID NOs: 23 and 24). The DNAs encoding the above variable regions were synthesized by Shanghai Sango Biotech Co., Ltd. The heavy chain variable region of Atezolizumab (Atezolizumab-VH) was connected to the human IgG1 heavy chain constant region (SEQ ID NO: 11) to obtain a full-length heavy chain gene, named Atezolizumab-HC; the light chain variable region of Atezolizumab (Atezolizumab-VL) was connected to the human Kappa light chain constant region (SEQ ID NO: 12) to obtain a full-length light chain gene, named Atezolizumab-LC. Atezolizumab-HC and Atezolizumab-LC were constructed into the pcDNA4 expression vector, respectively, and the antibody was expressed and purified. The obtained antibody was named Atezolizumab-IgG1.

Example 1.5

Determination of the Relative Affinity of Humanized anti-human PD-L1 Antibody to PD-L1 by ELISA An ELISA plate was coated with the above PD-L1-His with a coating concentration of 10 ng/well, and blocked with PBST containing 1% BSA. The antibody to be tested was serially diluted, and then transferred to the above plate coated with recombinant protein, incubated at room temperature for half an hour and then the plate was washed; an appropriately diluted HRP-labeled goat anti-mouse antibody (Fc-Specific) (purchased from Sigma) was added, incubated at room temperature for half an hour and then the plate was washed; 100 µl of chromogenic solution with TMB as a substrate was added to each well, incubated at room temperature for 1-5 min; 50 µl of stop solution (2M $H_2SO_4$) was added to stop the reaction. OD450 values were read with a microplate reader (SpectraMax 190), and graphing and data analysis were performed using GraphPad Prism6, and EC50 values were calculated.

Figure 2:
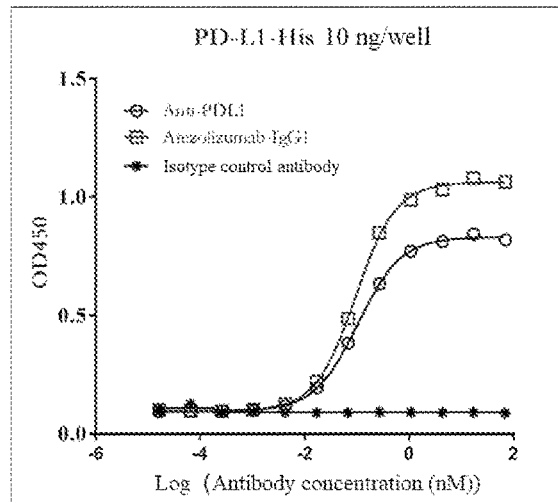
FIG. 2 shows the ELISA results of the relative affinity of Anti-PDL1 to PD-L1.

As shown in FIG. 2, both Anti-PDL1 and Atezolizumab-IgG1 can effectively bind to PD-L1-His, with EC50s of 0.1018 nM and 0.09351 nM, respectively, and their apparent affinities are equivalent. The isotype control antibody is a human IgG1 antibody that does not bind to human PD-L1.

Example 1.6

Determination of the Ability of Humanized Anti-Human PD-L1 Antibody to Block PD-1/PD-L1 Interaction PD-L1-ECD-hFc was biotinylated with Biotin N-hydroxysuccinimide ester (purchased from Sigma, Cotolog No./Specification: H1759-100MG). Human PD-1-ECD-hFc was diluted to 2 µg/ml with sodium carbonate buffer (1.59 g $Na_2CO_3$ and 2.93 g $NaHCO_3$ dissolved in 1 L of pure water), and added into a 96-well ELISA plate with a multichannel pipette at 100 μl/well, incubated at room temperature for 4 h; washed once with PBST, blocked with PBST containing 1% BSA at 200 μl/well, incubated at room temperature for 2 h; the blocking solution was discarded, the plate was patted dry, and placed at 4° C. for later use. The biotinylated PD-L1-ECD-hFc was diluted to 500 ng/ml with PBST solution containing 1% BSA in a 96-well plate; the anti-human PD-L1 antibody was serially diluted with the above protein solution; the above diluted antibody and the biotinylated PD-L1-ECD-hFc were mixed and transferred to the above ELISA plate coated with human PD1-ECD-hFc, and incubated at room temperature for 1 hour; the plate was washed 3 times with PBST; Streptavidin-HRP (purchased from BD Biosciences) diluted 1:1000 in PBST with 1% BSA was added, and incubated at room temperature for 45 min; the plate was washed 3 times with PBST; chromogenic solution (with TMB as a substrate) was added at 100 μl/well, incubated at room temperature for 1-5 min; stop solution (2M $H_2SO_4$) was added at 50 μl/well to stop the chromogenic reaction. OD450 values were read with a microplate reader (SpectraMax 190). Graphing and data analysis were performed using GraphPad Prism6, and IC50 values were calculated.

Figure 3:
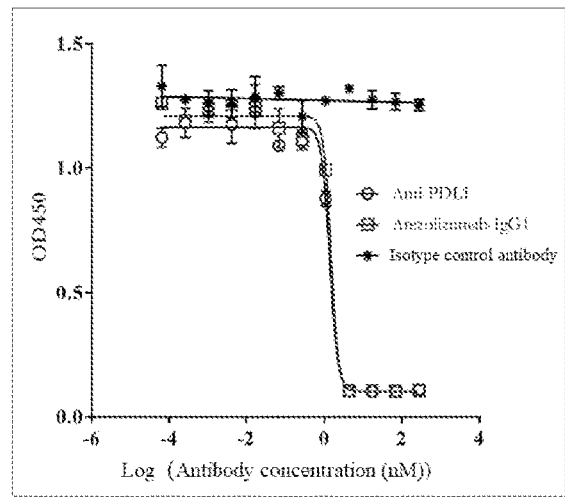
FIG. 3 shows results of the ability of Anti-PDL1 to block the interaction of PD-1/PD-L1.

As shown in FIG. 3, both Anti-PDL1 and Atezolizumab-IgG1 can effectively block the interaction between PD-1 and PD-L1, with IC50s of 1.366 nM and 1.471 nM, respectively, and their blocking abilities are equivalent. The isotype control antibody is a human IgG1 antibody that does not bind to human PD-L1.

Example 1.7

Figure 4A:
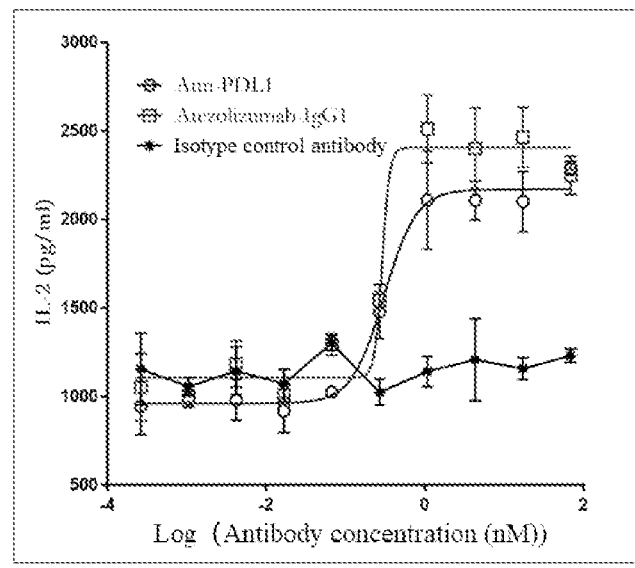
FIGS. 4A and 4B show the evaluation results of the ability of Anti-PDL1 to enhance MLR.
Figure 4B:
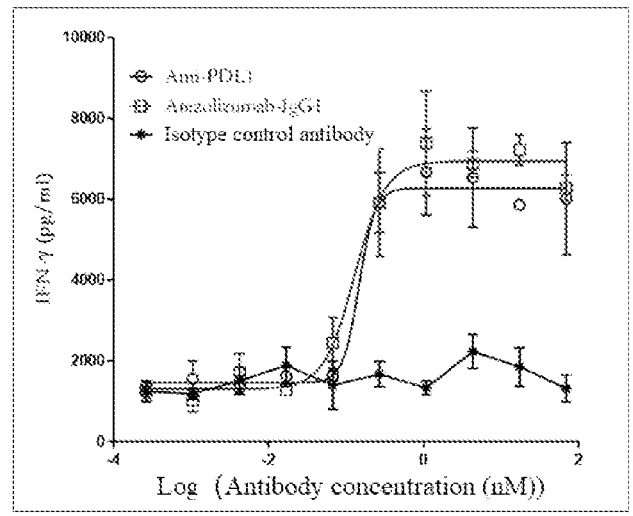

Determination of the Functional Activity of Humanized Anti-Human PD-L1 Antibody by Mixed Lymphocyte Reaction As shown in FIG. 4A, both Anti-PDL1 and Atezolizumab-IgG1 can effectively stimulate MLR to secrete IL-2, with EC50s of 0.306 nM and 0.29 nM, respectively. As shown in FIG. 4B, both Anti-PDL1 and Atezolizumab-IgG1 can effectively stimulate MLR to secrete IFN-γ, with EC50s of 0.1464 nM and 0.1294 nM, respectively. The isotype control antibody is a human IgG1 antibody that does not bind to human PD-L1.

Example 2

Construction of the Tetravalent Bispecific Antibody Against PD-1 and PD-L1

Example 2.1

Sequences

MAb1-25-Hu (hereinafter referred to as 609) is a humanized anti-human PD-1 monoclonal antibody, the sequences of heavy chain variable region and light chain variable region of which are described in WO2018/137576A1. Humanized heavy chain variable region and light chain variable region (SEQ ID NOs: 25 and 26) were connected to the human IgG4 (S228P) heavy chain constant region (SEQ ID NO: 27) and Kappa light chain constant region (SEQ ID NO: 12), respectively, to finally obtain the heavy and light chain amino acid sequences of the complete humanized monoclonal antibody mAb1-25-Hu (609).

Anti-PDL1 is a humanized monoclonal antibody of anti-human PD-L1, and its sequence is shown in Example 1.3.

Example 2.2

Selection of Common Light Chain

BLAST (Basic Local Alignment Search Tool) was used to compare the amino acid sequences of the light chain variable region of Anti-PDL1 and the light chain variable region of 609. The results show that between them, the identical amino acids accounted for 74% (Identities) and the amino acids with similar properties accounted for 86% (Positives).

The heavy chain and light chain genes of Anti-PDL1 were named Anti-PDL1-HC and Anti-PDL1-LC, and the heavy chain and light chain genes of 609 were named 609-HC and 609-LC, respectively. They were constructed into the pcDNA4 expression vector, respectively. The above heavy chain and light chain expression vectors were combined in the following manner Anti-PDL1-HC+Anti-PDL1-LC, 609-HC+609-LC, Anti-PDL1-HC+609-LC and 609-HC+ Anti-PDL1-LC, and the antibodies were expressed and purified. The obtained antibodies were named Anti-PDL1, 609, Anti-PDL1-HC+609-LC and 609-HC+Anti-PDL1-LC, respectively.

ELISA plates were coated with the above PD1-ECD-hFc and PD-L1-ECD-hFc with a coating concentration of 10 ng/well, respectively. The plates were blocked with PBST containing 1% BSA. The antibodies to be tested were serially diluted, then transferred to the above plates coated with recombinant proteins, incubated at room temperature for half an hour and then the plates were washed; an appropriately diluted HRP-labeled goat anti-human antibody (Fc-Specific) (purchased from Sisgma) was added, incubated at room temperature for half an hour and then the plates were washed; chromogenic solution with TMB as a substrate was added at 100 μl/well, incubated at room temperature for 1~5 min; 50 μl of stop solution (2M $H_2SO_4$) was added to stop the reaction. OD450 values were read with a microplate reader (SpectraMax 190). Graphing and data analysis were performed using GraphPad Prism6, and EC50 values were calculated.

Figure 5A:
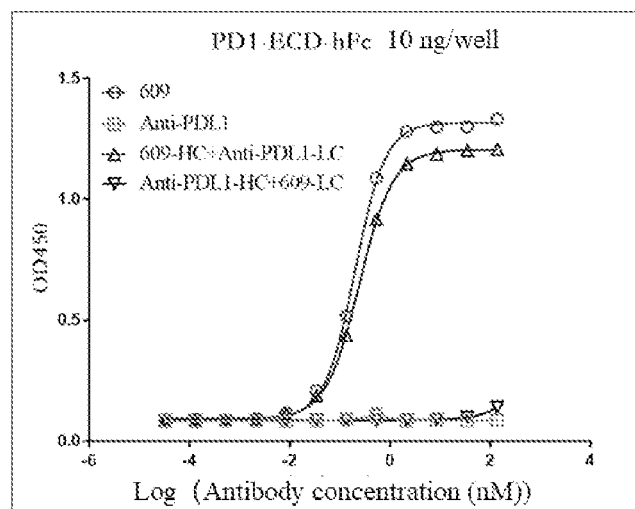
FIGS. 5A and 5B show the ELISA results of Anti-PDL1 and 609 and their hybrid antibodies.
Figure 5B:
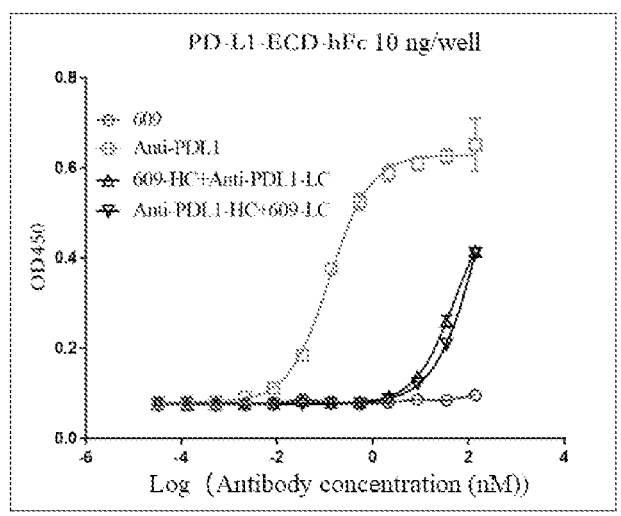

As shown in FIG. 5A, 609 and 609-HC+Anti-PDL1-LC can effectively bind to PD1-ECD-hFc, with EC50s of 0.2001 nM and 0.2435 nM, respectively; while Anti-PDL1 and Anti-PDL1-HC+609-LC cannot binds to PD1-ECD-hFc. As shown in FIG. 5B, Anti-PDL1 can effectively bind to PD-L1-ECD-hFc, with an EC50 of 0.1246 nM, while 609, Anti-PDL1-HC+609-LC and 609-HC+Anti-PDL1-LC cannot effectively bind to PD1-ECD-hFc. Here, Anti-PDL1-LC (SEQ ID NOs: 15 and 16) was selected as the common light chain to construct a bispecific antibody.

Example 2.3

Construction of Bispecific Antibodies

The heavy chain variable region of Anti-PDL1 was connected to the CH1 domain of human IgG4, and then connected to the heavy chain variable region of 609 through an artificial linker (the linker used here is three GGGGS in series, SEQ ID NO: 28), and finally connected to the heavy chain constant region of human IgG4 (CH1+CH2+CH3, with S228P mutation in the hinge region). The long heavy chain gene containing two heavy chain variable regions and two CH1 domains constructed by this program was named PDL1-Fab-609-IgG4 (SEQ ID NOs: 29 and 30). Similarly, the heavy chain variable region of 609 was connected to the CH1 domain of human IgG4, and then connected to the heavy chain variable region of Anti-PDL1 through an artificial linker (the linker used here is three GGGGS in series, SEQ ID NO: 28), and finally connected to the heavy chain constant region of human IgG4 (CH1+CH2+CH3, with S228P mutation in the hinge region). The long heavy chain gene containing two heavy chain variable regions and two CH1 domains constructed by this program was named 609-Fab-PDL1-IgG4 (SEQ ID NOs: 31 and 32).

The above sequences were constructed into the pcDNA4 expression vector, respectively, the expression vectors of PDL1-Fab-609-IgG4 and 609-Fab-PDL1-IgG4 were combined with the Anti-PDL1-LC expression vector, and the antibodies were expressed and purified. The obtained antibodies were named PDL1-Fab-609-IgG4 and 609-Fab-PDL1-IgG4, respectively (for brevity, here only the name of the heavy chain is used as the name of the antibody).

Example 2.4

Determination of the Relative Affinity by ELISA

The determination method by ELISA refers to the description in Example 1.3.

Figure 6A:
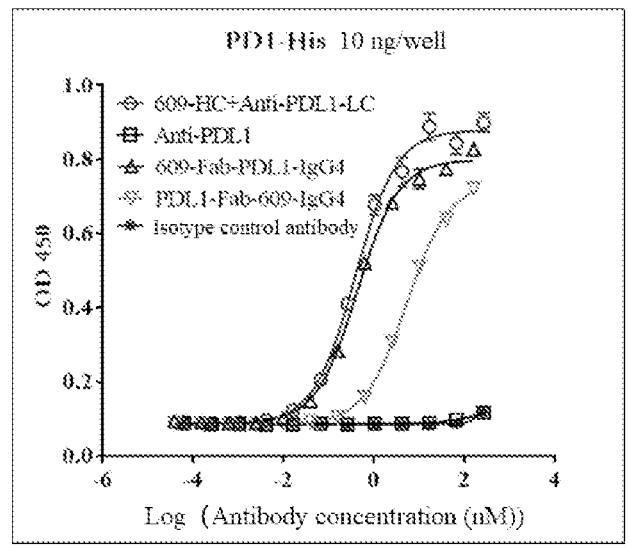
FIGS. 6A and 6B show the ELISA results of PDL1-Fab-609-IgG4 and 609-Fab-PDL1-IgG4.
Figure 6B:
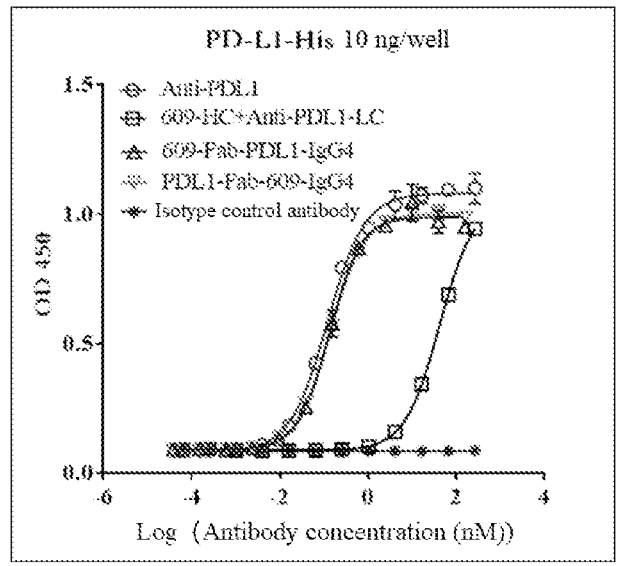

As shown in FIG. 6A, 609-HC+Anti-PDL1-LC, PDL1-Fab-609-IgG4 and 609-Fab-PDL1-IgG4 can effectively bind to PD1-His, with EC50s of 0.3821 nM, 5.308 nM and 0.4213 nM, respectively. As shown in FIG. 6B, Anti-PDL1, PDL1-Fab-609-IgG4 and 609-Fab-PDL1-IgG4 can effectively bind to PD-L1-His, with EC50s of 0.1204 nM, 0.1400 nM and 0.1350 nM, respectively. The isotype control antibody is a human IgG4 antibody that binds neither PD-1 nor PD-L1. The above results show that PDL1-Fab-609-IgG4 and 609-Fab-PDL1-IgG4 can bind to both PD-1 and PD-L1, indicating that they are bispecific antibodies.

Example 2.5

Evaluation of the Ability to Enhance MLR

Figure 7A:
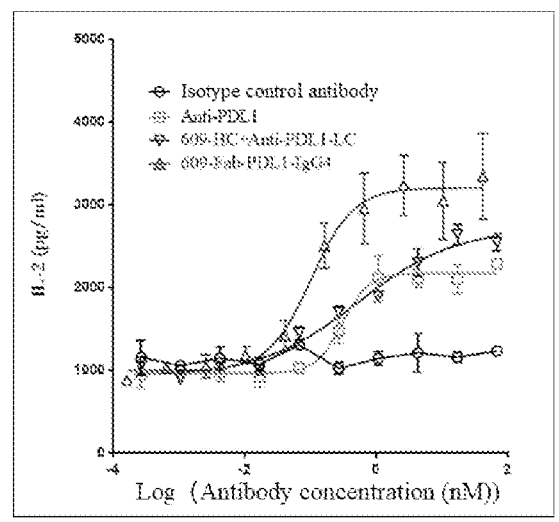
FIGS. 7A-7D show the evaluation results of the ability of 609-Fab-PDL1-IgG4 to enhance MLR.
Figure 7B:
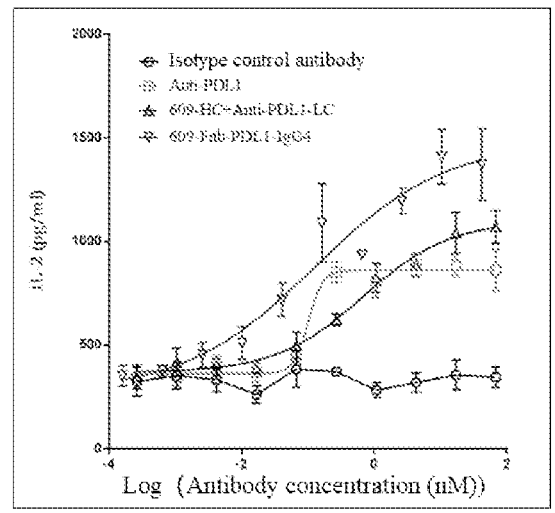
Figure 7C:
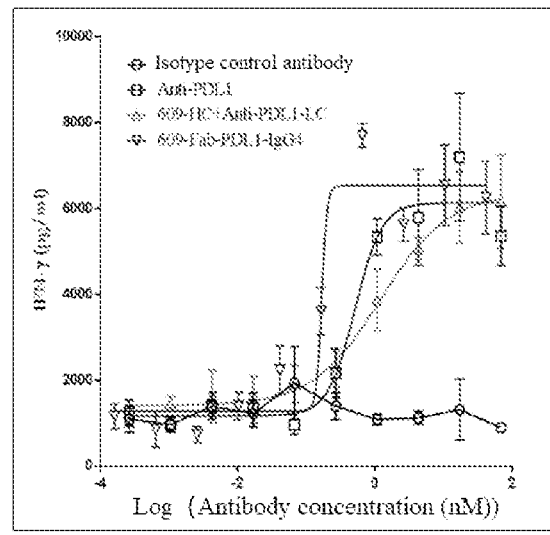
Figure 7D:
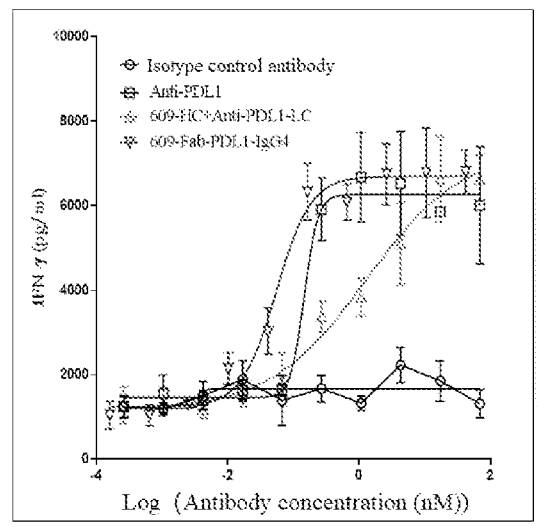

The results of A and C are from the same MLR experiment, and the results of B and D are from another independent MLR experiment, where the isotype control antibody is a human IgG4 antibody that binds neither PD-1 nor PD-L1. As shown in FIGS. 7A and 7B, Anti-PDL1, 609-HC+Anti-PDL1-LC and 609-Fab-PDL1-IgG4 can effectively stimulate MLR to secrete IL-2, with EC50s of 0.306 nM, 0.5384 nM, and 0.1023 nM in FIG. 7A, and EC50s of 0.1016 nM, 0.6819 nM, and 0.1259 nM in FIG. 7B, respectively. In addition, as shown in FIGS. 7C and 7D, Anti-PDL1, 609-HC+Anti-PDL1-LC and 609-Fab-PDL1-IgG4 can effectively stimulate MLR to secrete IFN-γ, with EC50s of 0.5119 nM, 1.21 nM and 0.1675 nM in FIG. 7C, and E50s of 0.1464 nM, 1.29 nM and 0.05491 nM in FIG. 7D, respectively. In addition, FIGS. 7A and 7B show that at a same concentration, compared to the monoclonal antibody Anti-PDL1 or 609-HC+Anti-PDL1-LC, 609-Fab-PDL1-IgG4 can stimulate MLR to secrete more IL-2.

Example 2.6

Determination of the Affinity by Biacore

Herein, the affinity of the above antibodies to PD-1 or PD-L1 was determined by Biacore 8K (GE healthcare). On Biacore 8K, the chip coupled with Protein A/G was used to capture various antibodies, respectively, and then the recombinant protein PD1-His or PD-L1-His was injected to obtain the binding-dissociation curve, which was eluted with 6M guanidine hydrochloride regeneration buffer for next cycle. Data were analyzed using the Biacore 8K Evaluation Software. The results are shown in Table 2.

TABLE 2-1

Binding and dissociation kinetic parameter and equilibrium dissociation constant for PD-1

| Sample name | Kon (1/Ms) | Koff (1/s) | KD (M) |
| --- | --- | --- | --- |
| 609-Fab-PDL1-IgG4 | 1.73E+05 | 4.43E−03 | 2.57E−08 |
| 609-HC + Anti-PDL1-LC | 1.26E+05 | 4.39E−03 | 3.49E−08 |

TABLE 2-2

Binding and dissociation kinetic parameter and equilibrium dissociation constant for PD-L1

| Sample name | Kon (1/Ms) | Koff (1/s) | KD (M) |
| --- | --- | --- | --- |
| 609-Fab-PDL1-IgG4 | 1.85E+06 | 1.12E−03 | 6.08E−10 |
| Anti-PDL1 | 1.63E+06 | 1.38E−03 | 8.43E−10 |

The experimental results show that 609-Fab-PDL1-IgG4 and 609-HC+Anti-PDL1-LC have very similar binding constants (Kon) and dissociation constants (Koff) for PD-1, and have basically equivalent equilibrium dissociation constants (KD), with KDs of 2.57E-08 and 3.49E-08, respectively. 609-Fab-PDL1-IgG4 and 609-HC+Anti-PDL1-LC also have very similar binding constants (Kon) and dissociation constants (Koff) for PD-L1, and have basically equivalent equilibrium dissociation constants (KD), with KDs of 6.08E-10 and 8.43E-10, respectively. The equilibrium dissociation constant (KD) is inversely proportional to the affinity.

Example 2.7

Pharmacokinetic Study

In this example, SD (Sprague-Dawley) rats (purchased from Zhejiang Vital River Laboratory Animal Technology Co., Ltd.) were used for the pharmacokinetic study of 609-Fab-PDL1-IgG4. There were five rats in each group, weighing about 200 g. Each rat was administered 1 mg of antibody by intravenous injection; blood was taken from the orbit at a specific time after the administration, and the blood was spontaneously coagulated and then centrifuged to obtain the serum.

The method of measuring the concentration of the target antibody in the serum is as follows: ELISA plates were coated with PD1-His and PD-L1-His, respectively, with the coating concentrations of 20 ng/well and 10 ng/well, respectively. The ELISA plates were blocked with PBST containing 1% bovine serum albumin An appropriately diluted rat serum was transferred to the above ELISA plates coated with PD1-His and PD-L1-His, incubated at room temperature for 1 hour, and the plates were washed, and then HRP-labeled goat anti-human (Fc-Specific) antibody (purchased from Sigma; this antibody has been treated with species cross-adsorption and does not recognize rat antibodies) was added, incubated at room temperature for half an hour, and the plates were washed; chromogenic solution with TMB as a substrate was added at 100 μl/well, incubated at room temperature for 1-5 min; 50 μl of stop solution (2M $H_2SO_4$) was added to stop the reaction. OD450 values were read with a microplate reader, and the OD450 was converted into antibody serum concentration using standard curve. Graphing and data analysis were performed using GraphPad Prism6. The half-life of the antibody in rats was calculated using the Phoenix software.

Figure 8A:
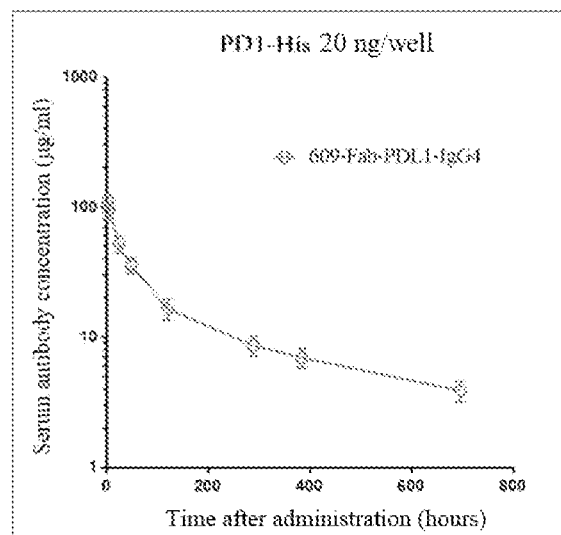
FIGS. 8A and 8B show the pharmacokinetic results of 609-Fab-PDL1-IgG4.
Figure 8B:
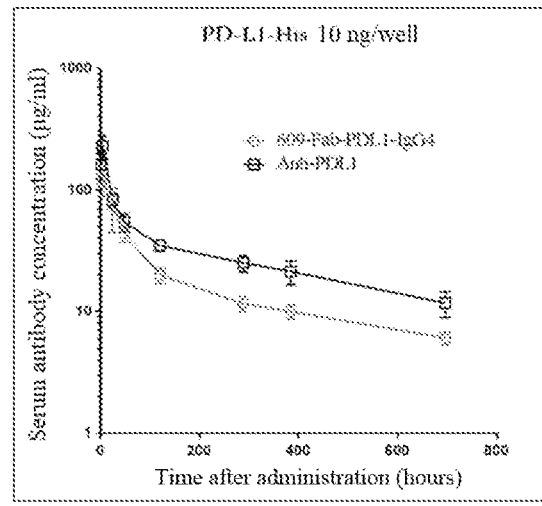

According to FIG. 8A, the half-life of 609-Fab-PDL1-IgG4 was 365 hours (15.2 days). According to FIG. 8B, the half-life of 609-Fab-PDL1-IgG4 was 446 hours (18.6 days), and the half-life of the monoclonal antibody Anti-PDL1 was 361 hours (15.0 days). The above results indicate that 609-Fab-PDL1-IgG4 has similar pharmacokinetic properties to the monoclonal antibody Anti-PDL1.

Example 2.8

Characterization of the Physicochemical Properties
Example 2.8.1 HPLC-SEC

Figure 9A:
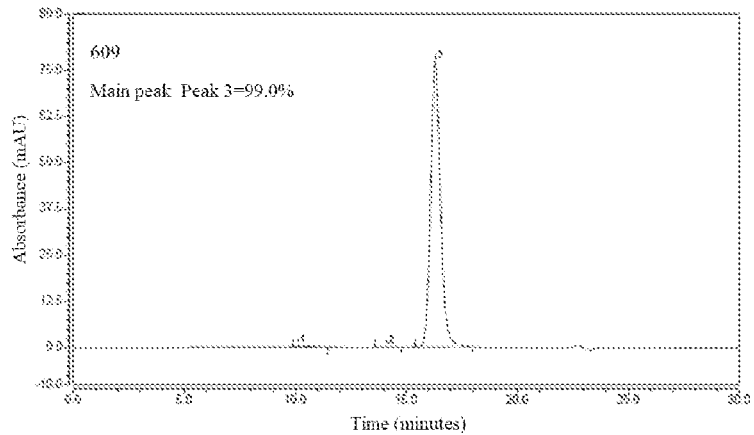
FIGS. 9A and 9B show the HPLC-SEC patterns of 609-Fab-PDL1-IgG4.
Figure 9B:
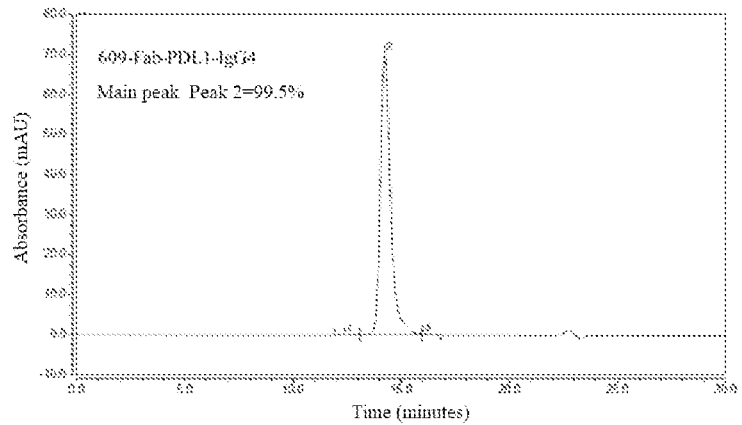

FIG. 9A shows the HPLC-SEC pattern of the monoclonal antibody 609, in which there are 3 obvious peaks, Peak 1, Peak 2 and Peak 3, accounting for 0.7%, 0.3% and 99.0%, respectively. Among them, the retention time of Peak1 and Peak 2 was less than that of Peak 3, indicating that Peak1 and Peak 2 may be produced by aggregates, and the sum of them accounts for 1.0%; there was no peak that may represent degraded fragments or incompletely assembled molecules in the pattern. FIG. 9B shows the HPLC-SEC pattern of 609-Fab-PDL1-IgG4, in which there are 3 obvious peaks, Peak 1, Peak 2, and Peak3, accounting for 0.2%, 99.5%, and 0.3%, respectively. The retention time of Peak1 was less than that of Peak 2, indicating that Peak 1 may be produced by aggregates; the retention time of Peak3 was more than that of Peak 2, indicating that Peak 3 may be produced by degraded fragments or incompletely assembled molecules.

Example 2.8.2 CE-SDS

Figure 10A:
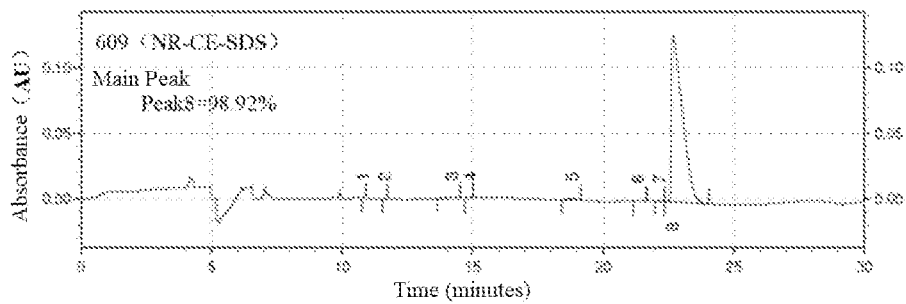
FIGS. 10A-10D show the CE-SDS patterns of 609-Fab-PDL1-IgG4.
Figure 10B:
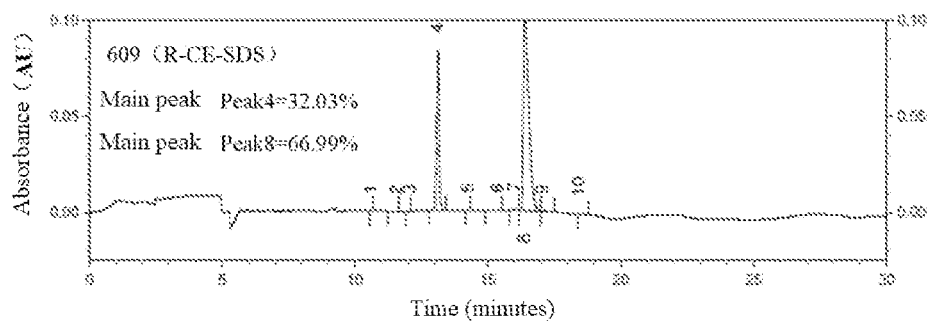
Figure 10C:
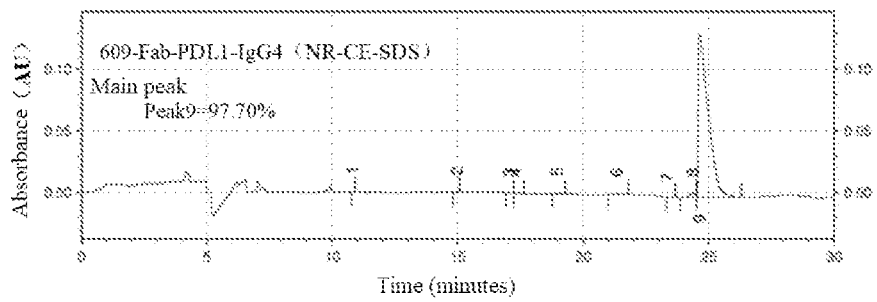
Figure 10D:
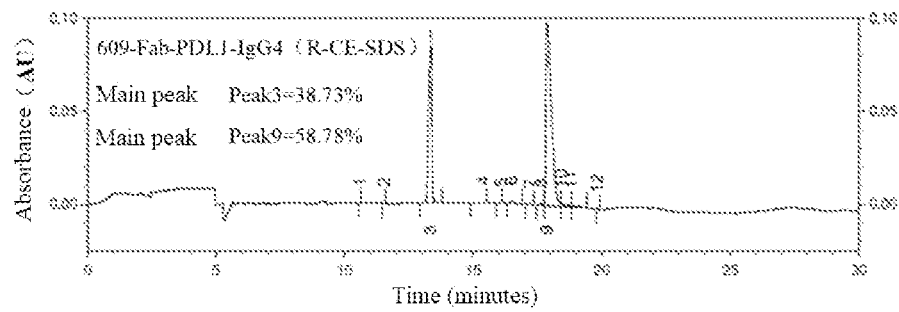

FIGS. 10A and 10B show the NR-CE-SDS and R-CE-SDS patterns of 609 mAb, respectively, and FIGS. 10C and 10D show the NR-CE-SDS and R-CE-SDS patterns of 609-Fab-PDL1-IgG4, respectively. Peak 8, the main peak in NR-CE-SDS of 609, accounted for 98.92%, and Peak 9, the main peak in NR-CE-SDS of 609-Fab-PDL1-IgG4, accounted for 97.70%. Peak 4 (corresponding to the light chain) and Peak 8 (corresponding to the heavy chain), the main peaks in R-CE-SDS of 609, accounted for 32.03% and 66.99%, respectively, and the ratio of the two peak areas was 1:2.09. Peak 3 (corresponding to the light chain) and Peak 9 (corresponding to the heavy chain), the main peaks in R-CE-SDS of 609-Fab-PDL1-IgG4, accounted for 38.73% and 58.78%, respectively, and the ratio of the two peak areas was 2:3.03. In NR-CE-SDS, the proportions of the main peaks of the 609 mAb and 609-Fab-PDL1-IgG4 were very similar; in R-CE-SDS, the peak area ratios of the light chain and heavy chain of the 609 mAb and 609-Fab-PDL1-IgG4 were consistent with expectations.

Example 2.8.3 HPLC-IEC

Figure 11A:
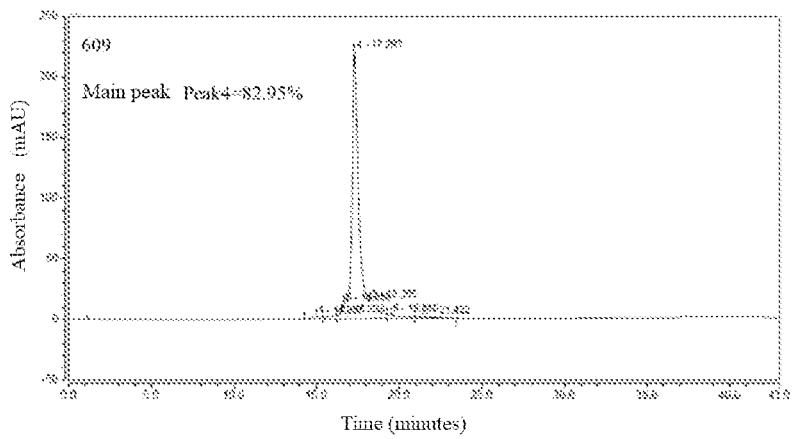
FIGS. 11A and 11B show the HPLC-IEC patterns of 609-Fab-PDL1-IgG4.
Figure 11B:
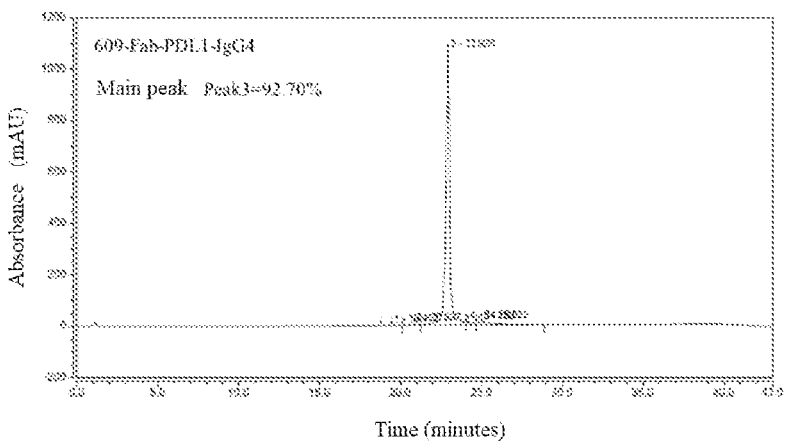

FIGS. 11A and 11B show the HPLC-IEC patterns of 609 and 609-Fab-PDL1-IgG4, respectively. Their main peaks accounted for 82.95% and 92.70%, respectively. The results show that the charge heterogeneity of 609-Fab-PDL1-IgG4 is better than that of the 609 mAb.

Example 2.8.4 DSC

Figure 12A:
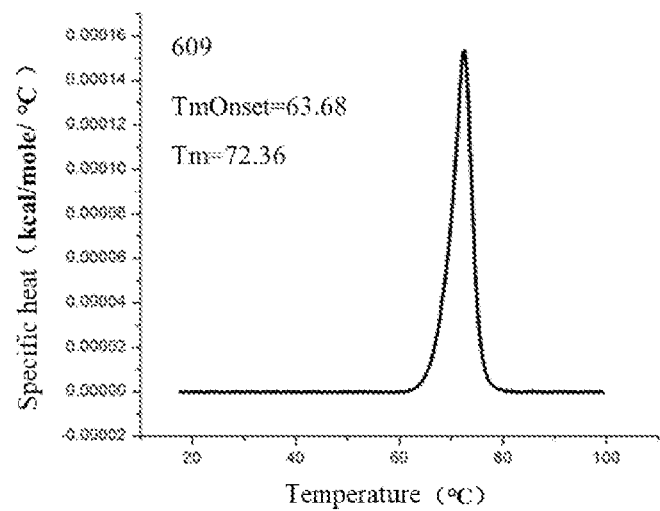
FIGS. 12A and 12B show the DSC patterns of 609-Fab-PDL1-IgG4.
Figure 12B:
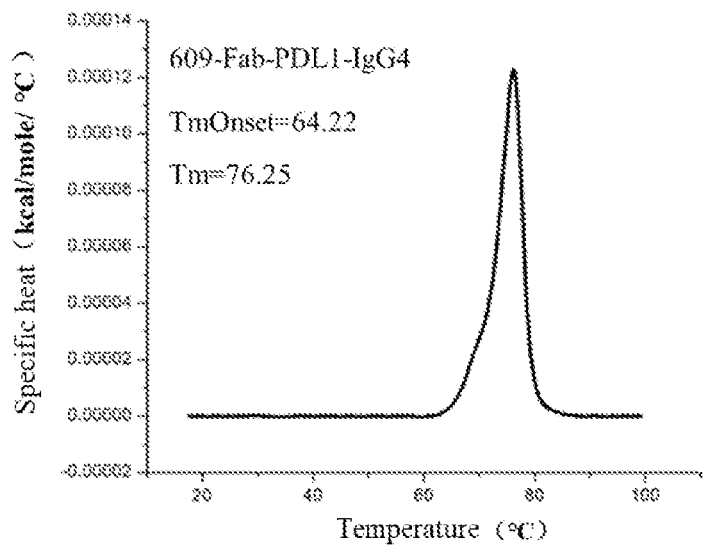

FIGS. 12A and 12B show the DSC patterns of 609 and 609-Fab-PDL1-IgG4, respectively. Among them, TmOnset represents the temperature at which the protein begins to unfold or denature, and Tm corresponds to the peak top temperature. The TmOnset and Tm of 609 were 63.68° C. and 72.36° C., and the TmOnset and Tm of 609-Fab-PDL1-IgG4 were 64.22° C. and 76.25° C., respectively. The above results indicate that 609 and 609-Fab-PDL1-IgG4 have very similar thermal stability.

Example 2.8.5 Detection of Molecular Weight

Figure 13:
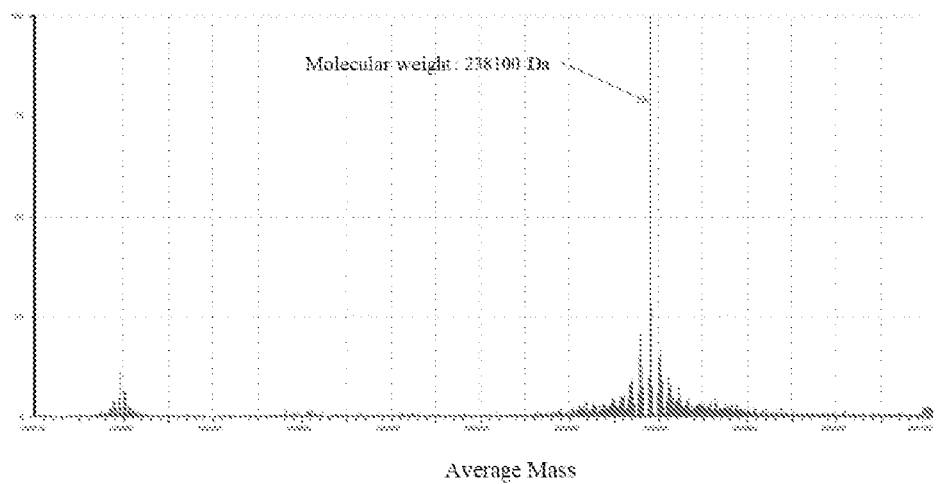
FIG. 13 shows the mass spectrum pattern of 609-Fab-PDL1-IgG4.

Each molecule of 609-Fab-PDL1-IgG4 contains two long heavy chains and four light chains. The calculation of the expected molecular weight took into account the modification of the C-terminal lysine residue of the heavy chain, being 238,099Da. As shown in FIG. 13, the measured molecular weight was 238,100 Da, which only differs by 1 Da from the expected molecular weight. The above results indicate that the molecular structure of 609-Fab-PDL1-IgG4 is consistent with expectations.

Example 3

Anti-Tumor Effect of the Bispecific Antibody Against PD-1 and PD-L1 In Mice

Figure 14:
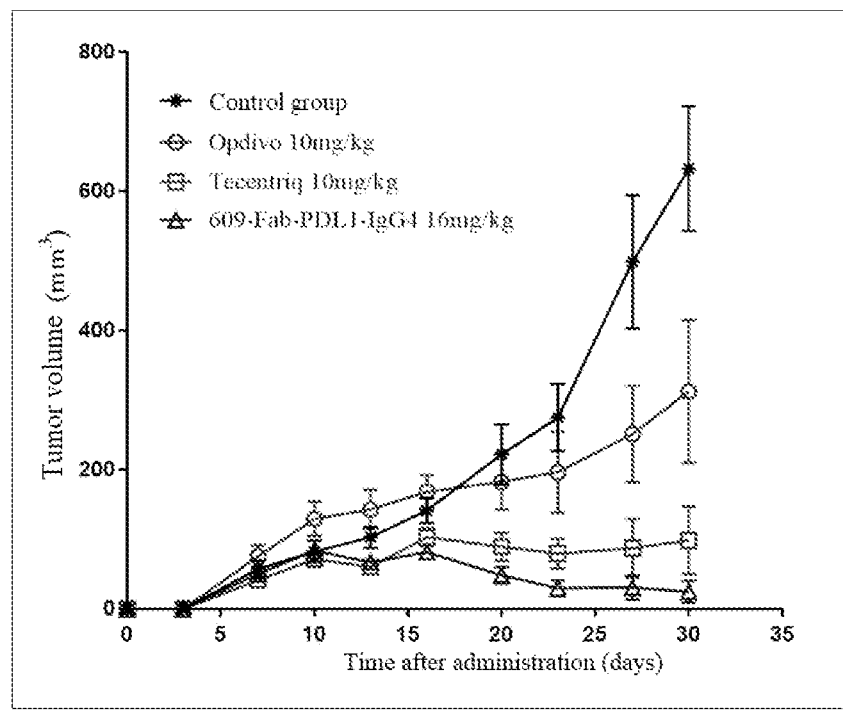
FIG. 14 shows the anti-tumor effect of the bispecific antibody 609-Fab-PDL1-IgG4 in mice.

Human peripheral blood mononuclear cells (PBMC) were used to rebuild the human immune system in NSG mice, and a human lung cancer NCI-H292 subcutaneous xenograft model was established on the mice. The mouse model had both T cells expressing human PD-1 and human tumor cells expressing human PD-L1, so it can be used to evaluate the anti-tumor activity of the bispecific antibody against PD-1 and PD-L1 in vivo. The specific procedures are as follows: human non-small cell lung cancer NCI-H292 cells (ATCC® $^{CRL}$1848™) cultured in vitro were collected, the cell suspension was adjusted to a concentration of $1\times10^8$/ml, and then mixed with Matrigel (purchased from BD Biosciences, Cat. No.: 356234) in equal volume. The purchased PBMC (purchased from Allcells, Cat. No.: PB005-C) was resuscitated in vitro, and the PBMC cells were resuspended in PBS, and the PBMC suspension was adjusted to a concentration of $1\times10^7$/ml. The mixed tumor cell suspension and the PBMC suspension were mixed in equal volume. Under sterile conditions, 200 μl of the mixed cell suspension was inoculated subcutaneously on the right upper back of M-NSG mice (purchased from Shanghai Model Organisms Center, Inc.). On the same day, the mice inoculated with mixed cells were randomly divided into groups according to their body weight, with 10 mice in each group. The drug treatment of mice in each group is as follows: Control group, injected with saline; Opdivo group, injected with 10 mg/kg of anti-PD-1 positive control antibody Opdivo (produced by Bristol-Myers Squibb); Tecentriq group, injected with 10 mg/kg of anti-PD-L1 positive control antibody Tecentriq (produced by Roche Pharmaceuticals); 609-Fab-PDL1-IgG4 group, injected with 16 mg/kg of 609-Fab-PDL1-IgG4. Taking into account the difference in molecular weight between bispecific antibodies and monoclonal antibodies, the dose of the drug in this experiment was provided according to the rule of equal amount of substance. Subsequently, the drugs were administered according to the above-designed plan, twice a week for a total of 8 times, and the tumor volumes were measured twice a week. Finally, the growth curve of tumor of each group determined over time is shown in FIG. 14.

The results show that at the end of the experiment on the 30th day, the tumor inhibition rates of Opdivo, Tecentriq and 609-Fab-PDL1-IgG4 were 50.5%, 84.4% and 96.0%, respectively (tumor inhibition rate=(average volume of control group-average volume of experimental group)/average volume of control group×100%). Compared to Opdivo and Tecentriq, 609-Fab-PDL1-IgG4 can inhibit tumor growth more effectively.

What is claimed is:

1. A tetravalent bispecific antibody against PD-1 and PD-L1, characterized in that, the tetravalent bispecific antibody comprises two identical polypeptide chains and four common light chains, wherein each of the two identical polypeptide chains has the amino acid sequence as shown in SEQ ID NO: 29 or SEQ ID NO: 31, and each of the four common light chains has the amino acid sequence as shown in SEQ ID NO: 15.

2. An isolated polynucleotide, characterized in that, the polynucleotide encodes the tetravalent bispecific antibody of claim 1.

3. The isolated polynucleotide of claim 2, characterized in that, the isolated polynucleotide encodes the two identical polypeptide chains and the four common light chains, wherein the isolated polynucleotide comprises a polynucleotide sequence encoding the two identical polypeptide chains as shown in SEQ ID NO: 30 or SEQ ID NO: 32, and a polynucleotide sequence encoding the four common light chains as shown in SEQ ID NO:16.

4. An expression vector, characterized in that, the expression vector comprises the isolated polynucleotide of claim 2.

5. A host cell, characterized in that, the host cell comprises the expression vector of claim 4.

6. A method of preparing the tetravalent bispecific antibody of claim 1, characterized in that, the method comprises the following steps:

a) culturing the host cell of claim 5 under expression conditions, to express the tetravalent bispecific antibody;

b) isolating and purifying the tetravalent bispecific antibody of step a).

7. A pharmaceutical composition, characterized in that, the pharmaceutical composition comprises the tetravalent bispecific antibody of claim 1 and a pharmaceutically acceptable carrier.

8. A method of treating cancer, characterized in that, the method comprises administering the tetravalent bispecific antibody of claim 1 or the pharmaceutical composition of claim 7 to a subject in need.

9. The method of claim 8, characterized in that, the cancer is selected from the group consisting of melanoma, kidney cancer, prostate cancer, pancreatic cancer, breast cancer, colon cancer, lung cancer, esophageal cancer, head and neck squamous cell carcinoma, liver cancer, ovarian cancer, cervical cancer, thyroid cancer, glioblastoma, glioma, leukemia, lymphoma and other neoplastic malignant diseases.

10. An expression vector, characterized in that, the expression vector comprises the isolated polynucleotide of claim 3.

\* \* \* \* \*